United States Patent
Ashman et al.

(10) Patent No.: US 7,585,515 B2
(45) Date of Patent: Sep. 8, 2009

(54) CROSSLINKABLE POLYMERIC MATERIALS AND THEIR APPLICATIONS

(75) Inventors: Arthur Ashman, Westport, CT (US); V. Prasad Shastri, Nashville, TN (US)

(73) Assignee: A Enterprises, Inc., Westport, CT (US)

( * ) Notice: Subject to any disclaimer, the term of this patent is extended or adjusted under 35 U.S.C. 154(b) by 0 days.

(21) Appl. No.: 12/119,489

(22) Filed: May 12, 2008

(65) Prior Publication Data

US 2008/0318862 A1    Dec. 25, 2008

Related U.S. Application Data

(62) Division of application No. 10/789,442, filed on Feb. 26, 2004, now Pat. No. 7,393,493.

(60) Provisional application No. 60/450,538, filed on Feb. 27, 2003.

(51) Int. Cl.
*A61F 2/02* (2006.01)
*A61C 8/00* (2006.01)
*A61K 6/083* (2006.01)
*A61K 38/00* (2006.01)
*A61K 47/30* (2006.01)
*A61K 41/00* (2006.01)
*C08F 2/46* (2006.01)

(52) U.S. Cl. .......................... 424/423; 522/13; 522/14; 522/24; 522/26; 522/28; 522/48; 522/142; 523/114; 523/115; 433/228.1

(58) Field of Classification Search .................... 522/87, 522/24, 28, 107, 88, 13, 14, 26, 48, 142; 523/114, 115; 424/423; 433/228.1
See application file for complete search history.

(56) References Cited

U.S. PATENT DOCUMENTS

| 4,244,689 | A  | 1/1981  | Ashman |
| 4,969,906 | A  | 11/1990 | Kronman |
| 5,286,763 | A  | 2/1994  | Gerhart et al. |
| 5,529,914 | A  | 6/1996  | Hubbell et al. |
| 5,558,517 | A  | 9/1996  | Shalaby et al. |
| 5,837,752 | A  | 11/1998 | Shastri et al. |
| 5,902,599 | A  | 5/1999  | Anseth et al. |
| 6,313,189 | B1 | 11/2001 | Wenz et al. |
| 6,403,672 | B1 | 6/2002  | Randolph et al. |
| 6,579,532 | B1 | 6/2003  | Mandel et al. |
| 6,933,328 | B2 | 8/2005  | Schacht et al. |
| 7,393,493 | B2 | 7/2008  | Ashman et al. |

(Continued)

FOREIGN PATENT DOCUMENTS

WO    01/74411    10/2001

OTHER PUBLICATIONS

European Patent Office Communication; Jan. 29, 2009 (3pp).

*Primary Examiner*—Susan W Berman
(74) *Attorney, Agent, or Firm*—Darby & Darby P.C.; Lydia G. Olson

(57) ABSTRACT

The present invention relates to a novel composition for dental, orthopedic and drug delivery purpose. Specifically, it relates to composition comprising an admixture of a resorbable bone substitute and a crosslinkable prepolymer. It also relates to the composition formed by crosslinking the admixture.

30 Claims, 15 Drawing Sheets

U.S. PATENT DOCUMENTS

2003/0032733 A1    2/2003  Fisher et al.
2003/0180344 A1*   9/2003  Wise et al. .................. 424/423
2004/0091462 A1*   5/2004  Lin et al. ................... 424/93.7

* cited by examiner

Panarex view of failed algeport (T.C.P.) graft

Bioplant LC and regenerating bone

CROSSLINKABLE POLYMERIC MATERIALS AND THEIR APPLICATIONS

FIELD OF THE INVENTION

The present invention relates generally to materials which may be used in any part of the body as an implant or graft material. Specifically, the invention relates to crosslinkable polymeric materials which can promote the formation of bone and/or other tissue(s) and the applications for such materials.

BACKGROUND OF THE INVENTION

In the healing arts, there is often a need for an implant or graft material to replace, repair, or reconstruct tissues, in particular, hard tissues such as bone. For example, hard-tissue implant materials have been used in medicine and veterinary medicine as prosthetic bone materials to repair injured or diseased bone. Hard tissue implant materials are also used in the construction of prosthetic joints to fix the prosthetic joints to bones. In dental art, hard tissue implant materials are used in the reconstruction of jaw bone damages caused by trauma, disease or tooth loss; in the replacement or augmentation of the edentulous ridge; in the prevention of jaw bone loss by socket grafting; and in the treatment of periodontal bone void defects.

Specifically, in dental art, when a tooth is extracted, a large cavity is created in the alveolar bone. The alveolar bone begins to undergo resorption at a rate of 40-60% in 2-3 years, which continues yearly at a rate of 0.25% to 0.50% per year until death (Ashman A. et al., Prevention of Alveolar Bone Loss Post Extraction with HTR Grafting Material. *Oral Surg. Oral. Med. Oral. Pathol.* 60 (2):146-153, (1985)). Shifting of the remaining teeth, pocket formation, bulging out of the maxillary sinus, poor denture retention, loss of vertical dimension, formation of facial lines, unesthetic gaps between bridgework and gum are some of the undesirable consequences associated with such loss (Luc. W. J. Huys, Hard Tissue Replacement, *Dentist News*, (Feb. 15, 2002)). Such bone loss also creates a significant problem for the placement of dental implants to replace the extracted tooth. It has been reported in previous years that nearly 95% of implant candidates rejected were turned down because of inadequate height and/or width of the alveolar bone (Ashman A., Ridge Preservation, Important Buzzwords in Dentistry, *General Dentistry*, May/June, (2000)).

One proven technique for overcoming the bone and soft tissue problems associated with the extraction of the tooth is to fill the extraction site with a bone graft material (e.g., synthetic, bovine or cadaver derived), and cover the site with gum tissue (e.g., suturing closed) or a dental "bandage" (e.g., Biofoil® Protective Stripes) for a period of time sufficient for new bone growth. The cavity becomes filled with a mixture of the bone graft material acting as an osteoconductive scaffold for the newly regenerated/generated bone. When implant placement is desired, after a period of time sufficient to allow bone regeneration (or healing) in the cavity, a cylindrical bore drill can prepare the former extraction site, and a dental implant can be installed in the usual manner.

The problem associated with such technique is that, with most bone graft materials (e.g., cadaver- and bovine-derived), the dental implant cannot be installed immediately and placed in function with a suitable crown after the tooth extraction. Patients need to have repeated visits to the dentist's office, often waiting up to 6 months before a functional crown can be placed. In recent years, it has been reported that, with a few bone graft materials such as the Bioplant® HTR® detailed below, an implant can be placed immediately post-extraction (Ashman A. et al., Ridge Augmentation For Immediately Postextraction Implants: Eight-Year Retrospective Study, *The Regeneration Report*, 7(2), 85-95, (1995); Yukna R. A. et al., Evaluation of Hard Tissue Replacement Composite Graft Material as a Ridge Preservation/Augmentation Material in Conjunction with Immediate Hydroxyapatite-Coated Dental Implants, *J. Periodontol.*, pages 679-685, May 2003; and Yukna R. A. et al., HTR Synthetic Bone Grafts and Immediate Dental Implants, *Compendium of Continuing Education in Dentistry*, pages 649-657, September 2003, 24(9)). However, such immediate post-extraction implants were not immediately made functional with a crown to chew. A healing period of 4-8 months was typically required for bone generation around the implant before loading. In other words, for example, prior to the present invention, if a patient has to have a front tooth extracted and replaced, the best the dentist can do is to install a metal implant (e.g., titanium) immediately after the extraction, place a bone graft material (e.g., Bioplant® HTR® or a "barrier membrane") around the implant in the socket and send him home. A crown cannot be installed on top of the metal implant until the implant becomes load-bearing (i.e., osteointegrated), months after the implant placement. In the meantime, the patient does not have a functional (e.g., cannot chew) or an esthetically-pleasing replacement tooth.

Bone graft materials can be either organic (e.g., from cadavers or bovine), synthetic or a combination thereof.

Over the last decade, polymeric materials have been used widely as bone graft materials. These materials are bio-inert, biocompatible, can serve as a temporary scaffold to be replaced by host tissue over time, and can be degraded by hydrolysis or by other means to non-toxic products.

U.S. Pat. Nos. 4,535,485 ("the '485 patent") and 4,536,158 ("the '158 patent") disclose certain polymer-based implantable porous prostheses for use as bone or other hard tissue replacement which are composed generally of polymeric particles. Although the porous prostheses of the '485 and '158 patents have proven to be satisfactory for many applications in dentistry and orthopedics, there is room for improvement.

U.S. Pat. No. 4,728,570 ("the '570 patent") discloses a porous implant material which induces the growth of hard tissue. Based on the '570 patent, Bioplant Inc. (South Norwalk, Conn.) manufactures a slowly absorbable product called Bioplant® HTR® The Bioplant® HTR® has proven to be very useful in both preventing bone loss and stimulating bone generation. It has also been found suitable for esthetic tissue plumping as well as for immediate post-extraction implants as mentioned above. However, it still has the major problem associated with all bone graft material prior to the present invention; namely, the implant placed in an extraction socket or in edentulous spaces would not be immediately functional. A patient still must wait months for bone generation (e.g., osteointegration) to take place around the implant before revisiting the dentist's office months later to have a crown installed.

Within the last decade, polymers that are more biodegradable and/or bioresorbable than PMMA and PHEMA have been introduced into the field of tissue replacement.

Medical devices made with degradable polyesters such poly (L-lactic acid), poly(glycolic acid), and poly(lactic-co-glycolic acid) are approved for human use by the Food and Drug Administration, and have been used in many medical applications, for example, in sutures. These polymers, however, lack many properties necessary for restoring function in high load-bearing bone applications, since they undergo homogeneous, bulk degradation which is detrimental to the long-term mechanical properties of the material and leads to a large burst of acid products near the end of degradation (e.g., similar to inflammation). In contrast, surface eroding polymers (such as polyanhydrides) maintain their mechanical integrity during degradation and exhibit a gradual loss in size which permits bone ingrowth. However, linear polyanhydride systems have limited mechanical strength.

U.S. Pat. No. 5,837,752 ("the '752 patent") discloses a semi-interpenetrating polymer network ("semi-IPN") composition for bone repair comprising (1) a linear polymer selected from the group consisting of linear, hydrophobic biodegradable polymers and linear non-biodegradable hydrophilic polymers; and (2) one or more crosslinkable monomers or macromers containing at least one free radical polymerizable group, wherein at least one of the monomers or macromers includes an anhydride linkage and a polymerizable group selected from the group consisting of acrylate or methacrylate.

U.S. Pat. No. 5,902,599 ("the '599 patent") discloses biodegradable polymer networks which are useful in a variety of dental and orthopedic applications. Such biodegradable polymer networks can be formed by polymerizing anhydride prepolymers containing crosslinkable groups, such as unsaturated moieties. The anhydride prepolymers can be crosslinked, for example in a photopolymerization reaction by irradiation of the prepolymer with light in the presence of a photosensitive free radical initiator.

WO 01/74411 discloses a composition suitable for preparing a biodegradable implant comprised of a crosslinkable multifunctional prepolymer having at least two polymerizable terminal groups. It discloses placing a metal screw implant immediately into the extraction socket; firmly packing the void between the bone and the implant with a graft material such as the Bioplant® HTR®; applying a layer of the crosslinkable multifunctional prepolymer on top of the graft material and curing the layer to form a rigid collar around the metal implant. The cured ring around the neck of the implant allegedly resists the chewing forces on the implant that are mainly concentrated at the neck of the implant. However, the alleged support and resistance provided by such a cured ring is not sufficient in either the short or the long term, since the implant is only secured around the neck which is a very narrow area near the gum line. Hence, even if the cured ring is hardened, it does not provide adequate rigidity in the short term. In the long term, the cured ring does not have sufficient bone regenerating capability due to the lack of a bone stimulation material. Hence, the implant is not stable, still exhibits significant micromovement, and is not immediately load-bearing. Accordingly, WO 01/74411 does not teach, suggest or enable an immediately functional replacement tooth.

Therefore, there is a continued need in the replacement and restorative arts for materials and methods which reduce the time of the bone regenerative process, allow immediately functional dental implant, provide sufficient mechanical strength and/or minimize micromovement. In addition, there is a need to broaden the spectra of materials available for dental, orthopedic and drug delivery usage.

SUMMARY OF THE INVENTION

The present invention relates to a novel composition for dental, orthopedic and drug delivery purposes. Specifically, it relates to compositions comprising an admixture of a bone substitute and a crosslinkable prepolymer. Further, it relates to compositions formed by crosslinking the admixture.

Surprisingly, it has been discovered that the foregoing invention provides a curable admixture which immediately hardens upon curing and which becomes load-bearing so as to provide immediate support for the installation of a crown and immediate functionality for the artificial tooth.

The bone substitute can be an alloplast, autograft, allograft, xenograft or a mixture thereof. Preferably, it is an alloplast; more preferably a polymeric alloplast (porous or non-porous); even more preferably porous micron-sized particles, wherein each particle comprises a core layer comprised of a first polymeric material and a coating generally surrounding the core layer, the coating comprising a second polymeric material, wherein the second polymeric material is hydrophilic and has a composition different from the composition of the first polymeric material, and both polymeric materials are biocompatible.

Preferably, the diameter of the micron-sized particles is in the range of from about 250 microns to about 900 microns.

Preferably, the first polymeric material is polymethylmethacrylate, the second polymeric material is a polymeric hydroxyethylmethacrylate; and the composition further comprises a quantity of calcium hydroxide distributed on the internal and external surfaces of the micron-sized particles of the bone substitute. Upon exposure to aqueous solution (e.g., blood), calcium hydroxide is converted to a calcium carbonate apatite (bone) compound.

The crosslinkable prepolymer comprises a monomer and/or oligomer having polymerizable group(s) to crosslink to form a polymer network.

There are three embodiments for the crosslinkable prepolymer, with the first two being the most preferred, particularly when polyanhydrides are used. When cured, the hydrophobic nature of the polyanhydrides and the crosslinked structure keep water out of the interior of the polymer and allow for hydrolysis only at the surface. Hence, the polymer erodes only from the outside in. This type of degradation is particularly beneficial for dental, orthopedic and drug delivery applications because the cured composite will maintain structural integrity and/or mechanical integrity. In comparison, the polyorthoesters and polyacetals, etc., disclosed in the third embodiment below tend to degrade in a more homogenous fashion because they are more hydrophilic, not as tightly crosslinked, and more susceptible to water penetration. The biodegradable bonds in the third embodiment, therefore, cleave internally as well as externally, leading to a more rapid loss in strength at the outset.

In the first embodiment, the crosslinkable prepolymers comprises one or more anhydride(s) of i) a monomer or oligomer of a diacid or multifunctional acid and ii) a carboxylic acid molecule which includes a crosslinkable group, wherein the crosslinkable group is an unsaturated hydrocarbon moiety.

In the second embodiment, the crosslinkable prepolymer is a crosslinkable semi-IPN precursor comprising:

a) a linear polymer which is a hydrophobic biodegradable polymer or a non-biodegradable hydrophilic polymer; and b) at least one monomer or macromer containing at least one radically polymerizable group wherein at least one of the monomers or macromers includes an anhydride linkage and a polymerizable group which is an acrylate or methacrylate.

It is preferable that the hydrophobic biodegradable polymer be a polyanhydride.

In the third embodiment, the crosslinkable prepolymer comprises at least two polymerizable terminal groups and has a viscosity such that the crosslinkable prepolymer is deformable at a temperature of 0° to 60° C. into a three-dimensional shape and crosslinkable within the temperature range.

In all three embodiments above, the crosslinkable prepolymer may further comprise an initiator, preferably a photoinitiator, or a combination of a photoinitiator and a redox initiator system.

Optionally, the composition further comprises a therapeutic agent; a bone promoting agent, a porosity forming agent, and a diagnostic agent.

The curable admixture comprising the bone substitute and the crosslinkable prepolymer or the crosslinkable semi-IPN precursor is cured to form a cured composite.

The curable admixture and the cured composite are useful in the field of orthopedics, dentistry, and drug delivery. They can be used anywhere where bone or other tissue regeneration is required. When a therapeutic agent is incorporated in them, they are useful as drug delivery devices.

DETAILED DESCRIPTION OF THE INVENTION

Figure 1:
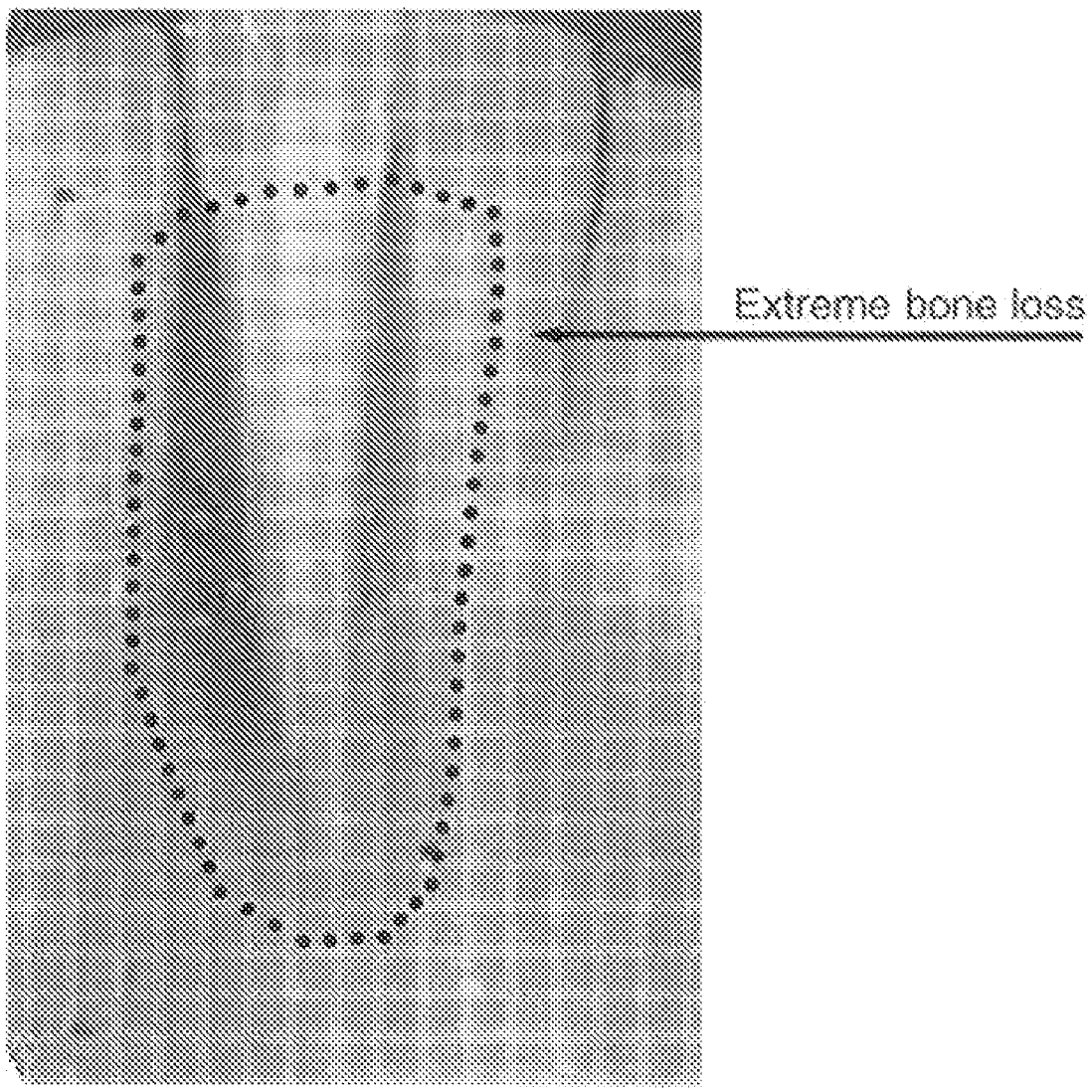
FIG. 1 represents the pre-operative X-ray of Patient A.

The present invention relates to a curable admixture and a cured composite formed from the curable admixture. The present invention also relates to methods of using the curable admixture and cured composite.

Curable Admixture and Cured Composite

The cured composite is formed by crosslinking the curable admixture. The curable admixture is formed by mixing a bone substitute and a crosslinkable prepolymer to form a substantially homogenous mixture. The admixture can be preformed or formed immediately before application.

Bone Substitute

The bone substitute can be any bone graft material known to one skilled in the art, preferably a polymeric one. It can be organic or synthetic or a combination thereof. Organic bone substitutes include autograft, allograft, xenograft or combinations thereof. Cadaver-derived materials are non-limiting examples of allografts. Bovine-derived materials (e.g., Osterograf® N-300 and Osterograf® N-700) are non-limiting examples of xenografts. Synthetic bone substitutes are also known as alloplasts. Non-limiting examples of the alloplast include calcium phosphate and calcium sulfate ceramics and polymeric bone graft materials. Preferably, the bone substitute comprises an alloplast; more preferably a polymeric alloplast.

The polymeric alloplast is preferably a plurality of micron-sized particles (preferably with a diameter from about 250 to 900 microns), each particle comprising a core layer comprised of a first polymeric material and a coating generally surrounding the core layer. The coating comprises a second polymeric material which is hydrophilic and has a composition different from the composition of the first polymeric material. Both polymeric materials in the polymeric alloplast are biocompatible. The first polymeric material is preferably an acrylic polymer; more preferably, poly(methyl methacrylate) (PMMA). The PMMA may further include a plasticizer, if desired. The second polymeric material is preferably a polymeric hydroxyethyl methacrylate (PHEMA). Preferred polymeric particles are disclosed in the '485 patent, the specification of which is hereby incorporated by reference in its entirety.

In a more preferred embodiment, the bone substitute is a plurality of calcium hydroxide-treated polymeric micron-sized particles. The quantity of calcium hydroxide is effective to induce the growth of hard tissue in the pores and on the surface of the polymeric micron-sized particles when packed in a body cavity. Preferably, the calcium hydroxide forms a coating on both the outer and inner surfaces of the polymeric particles.

The micron-sized particles of the bone substitute may further optionally include a non-bonding agent, such as barium sulfate, to prevent the particles from bonding together. Barium sulfate is also a radio-opaque compound and may be included so as to render the curable admixture and the cured composite visible on an X-ray radiograph. The calcium hydroxide also assists in preventing the polymeric particles from bonding together.

Preferred procedures for producing the bone substitute component of the curable admixture of the present invention are set forth in the specification of the '158 patent. Preferably, calcium hydroxide is introduced into the pores of the micron-sized particles by soaking the particles in an aqueous solution of calcium hydroxide, then removing any excess solution from the particles and allowing the particles to dry. Preferred aqueous solutions of calcium hydroxide have a concentration in the range of from about 0.05 percent to about 1.0 percent calcium hydroxide by weight.

In a most preferred embodiment, the bone substitute is Bioplant® HTR,® available from Bioplant Inc. (Norwalk, Conn.), set forth in the '570 patent, which is hereby incorporated by reference in its entirety. The Bioplant® HTR® are microporous particles of calcified ($Ca(OH)_2$/calcium-carbonate) copolymer of PMMA and PHEMA, with the outer calcium layer interfacing with bone forming calcium carbonate-apatite. The outer diameter of the particles is about 750 μm; the inner diameter is about 600 μm and the pore opening diameter is about 350 μm. Bioplant® HTR® is strong (forces greater than 50,000 lb/in will not crush the Bioplant® HTR® particles), biocompatible and negatively charged (−10 mV) to promote cellular attraction and resist infection.

Crosslinkable Prepolymer

The crosslinkable prepolymer comprises monomers and/or oligomers having polymerizable groups, preferably radically polymerizable groups, which crosslink to form a polymer network. Suitable polymerizable groups include unsaturated alkenes (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. The preferred polymerizable groups are acrylates, diacrylates, oligoacrylates, dimethacrylates, oligomethacrylates, and other biologically acceptable polymerizable groups. (Meth)acrylates are the most preferred active species polymerizable group.

These polymerizable groups can be present on hydrophobic or hydrophilic polymers, which can be used to adjust the hydrophobicity of the compositions. Non-limiting examples of suitable hydrophobic polymers include polyanhydrides, polyorthoesters, polyhydroxy acids, polydioxanones, polycarbonates, and polyaminocarbonates. Non-limiting examples of suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose (and derivatives), and hydroxyalkylated celluloses (and derivatives) such as hydroxyethyl cellulose and methylhydroxypropyl cellulose, and natural polymers such as polypeptides, polysaccharides or carbohydrates such as Ficoll® polysucrose, hyaluronic acid, dextran (and derivatives), heparan sulfate, chondroitin sulfate, heparin, or alginate, and proteins such as gelatin, collagen, albumin, or ovalbumin or copolymers or blends thereof.

Preferably, the monomer and/or oligomer comprises a biodegradable linkage such as amide-, anhydride-, carbonate-, ester-, or orthoester linkages; more preferably, an anhydride-linkage so that the polymer network formed by the monomer and/or oligomer is biodegradable.

Preferably, it further comprises an initiator, more preferably a photoinitiator or a combination of a photoinitiator and a redox initiator system.

The molecular weight of the crosslinkable prepolymer is preferably in the range of about 150 to about 20,000. Preferably, the prepolymer has from 1 to about 100 repeating units in the structure, more preferably from about 1 to about 20, and most preferably from about 1 to about 10 repeating units.

Three non-limiting embodiments of the crosslinkable prepolymer are disclosed below.

Details of First Embodiment of Crosslinkable Prepolymer

As a first preferred embodiment, the crosslinkable prepolymer is one or more anhydride monomers or oligomers. Useful monomers or oligomers include anhydrides of a diacid or multifunctional acids and carboxylic acid molecules which include a crosslinkable group such as an unsaturated moiety.

Preferably, the crosslinkable prepolymer is linear with an unsaturated hydrocarbon moiety at each terminus and comprises a dianhydride of a dicarboxylic acid monomer or oligomer and a carboxylic acid molecule comprising an unsaturated moiety. More desirably, it comprises a methacrylic acid dianhydride of a monomer or oligomer of a diacid selected from the group consisting of sebacic acid and 1,3-bis(p-carboxyphenoxy)-alkane such as 1,3-bis(p-carboxyphenoxy)-propane.

Exemplary diacids or multifunctional acids include sebacic acid, 1,3-bis(p-carboxyphenoxy)-alkanes such as 1,3-bis(p-carboxyphenoxy)-propane (MCPP) or 1,3-bis(p-carboxyphenoxy)-hexane (MCPH), dodecanedioic acid, fumaric acid, bis(p-carboxyphenoxy)methane, terephthalic acid, isophthalic acid, p-carboxyphenoxy acetic acid, p-carboxyphenoxy valeric acid, p-carboxyphenoxy octanoic acid, or citric acid. Preferably, it is sebacic acid or 1,3-bis(p-carboxyphenoxy)-alkanes.

Exemplary carboxylic acids include methacrylic acid, or other functionalized carboxylic acids, including, e.g., acrylic, methacrylic, vinyl and/or styryl groups. The preferred carboxylic acid is methacrylic acid.

The anhydride monomers or oligomers are formed, for example, by reacting the diacid with an activated form of the carboxylic acid, such as an anhydride thereof, to form an anhydride. A detailed description of the anhydride monomer(s) or oligomer(s) suitable as crosslinkable prepolymer(s) is provided in the '599 patent, the specification of which is incorporated by reference in its entirety.

Another route for synthesizing the methacrylated sebacic acid (MSA) and (1,3-bis(carboxyphenoxy))propyl dimethacrylate (CPPDM) is described by Tarcha, et al., *J. Polym. Sci, Part A, Polym. Chem.* (2001), 39, 4189.

In a preferred embodiment, the crosslinkable prepolymer is a mixture of a first anhydride and a second anhydride. The ratio of these anhydrides can be adjusted to provide the biodegradation, hydrophilicity and/or adherence properties most suitable for a specific application.

For example, polymer networks formed by crosslinking dimethacrylated anhydride monomers formed from sebacic acid typically biodegrade much faster than that formed from 1,3-bis(p-carboxyphenoxy)-alkane(s). Hence, mixing anhydrides formed from sebacic acid with anhydrides formed from 1,3-bis(p-carboxyphenoxy)-alkane(s) in various ratios provides a wide array of degradation behaviors.

The ratio of the first anhydride to the second anhydride can vary widely. Preferably, it is in the range from about 1:20 to about 20:1; more preferably from about 1:5 to about 5:1; even more preferably from about 1:5 to about 1:1, most preferably at about 1:1.

Preferably, as detailed below, the crosslinkable prepolymer comprises a photoinitiator or a combination of a photoinitiator and a redox initiator system.

Details of Second Embodiment of Crosslinkable Prepolymer

In the second embodiment, the crosslinkable prepolymer is a crosslinkable semi-IPN precursor.

The crosslinkable semi-IPN precursor comprises at least two components: the first component is a linear polymer, and the second component is one or more crosslinkable monomers or macromers. The crosslinkable semi-IPN precursor forms a semi-interpenetrating network ("semi-IPN") when crosslinked. Semi-IPNs are defined as compositions that include two independent components, where one component is a crosslinked polymer and the other component is a non-crosslinked polymer. The crosslinkable semi-IPN precursor and the semi-IPN it forms are described in detail in U.S. Pat. No. 5,837,752 to Shastri et al., which is incorporated by reference in its entirety.

The first component of the crosslinkable semi-IPN precursor is a linear polymer. Preferably, the linear polymer in the first component is (i) a linear hydrophobic biodegradable polymer, preferably a homopolymer or copolymer which includes hydroxy acid and/or anhydride linkages, or (ii) a linear, non-biodegradable hydrophilic polymer, preferably polyethylene oxide or polyethylene glycol.

Preferably, at least one of the monomers or macromers includes a degradable linkage, preferably an anhydride linkage. The linear polymer preferably constitutes between 10 and 90% by weight of the crosslinkable semi-IPN precursor composition, more preferably between 30 and 70% of the crosslinkable semi-IPN precursor composition.

Linear polymers are homopolymers or block copolymers that are not crosslinked. Hydrophobic polymers are well known to those of skill in the art. Examples of suitable biodegradable polymers include polyanhydrides, polyorthoesters, polyhydroxy acids, polydioxanones, polycarbonates, and polyaminocarbonates. Preferred polymers are polyhydroxy acids and polyanhydrides. Polyanhydrides are the most preferred polymers.

Linear, hydrophilic polymers are well known to those of skill in the art. Examples of suitable hydrophilic non-biodegradable polymers include poly(ethylene glycol), poly(ethylene oxide), partially or fully hydrolyzed poly(vinyl alcohol), poly(ethylene oxide)-co-poly(propylene oxide) block copolymers (poloxamers and meroxapols) and poloxamines. Preferred hydrophilic non-biodegradable polymers are poly(ethylene glycol), poloxamines, poloxamers and meroxapols. Poly(ethylene glycol) is the most preferred hydrophilic non-biodegradable polymer.

The second component of the crosslinkable semi-IPN precursor is one or more crosslinkable monomers or macromers. Preferably, at least one of the monomers or macromers includes an anhydride linkage. Other monomers or macromers that can be used include biocompatible monomers and macromers which include at least one radically polymerizable group. For example, polymers including alkene linkages which can be crosslinked may be used, as disclosed in WO 93/17669 by the Board of Regents, University of Texas System, the disclosure of which is incorporated herein by reference.

Suitable polymerizable groups include unsaturated alkenes (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. The preferred polymerizable groups are acrylates, diacrylates, oligoacrylates, dimethacrylates, oligomethacrylates, and other biologically acceptable polymerizable groups. (Meth)acrylates are the most preferred active species polymerizable group.

These functional groups can be present on hydrophobic or hydrophilic polymers, which can be used to adjust the hydrophobicity of the compositions. Suitable hydrophobic polymers include polyanhydrides, polyorthoesters, polyhydroxy acids, polydioxanones, polycarbonates, and polyaminocarbonates. Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof.

The polymers can be biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 daltons or below.

The polymers can include two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Methods for the synthesis of these polymers are well known to those skilled in the art. See, for example, Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Preferably, the monomers and/or macromers that include radically polymerizable groups include slightly more than one crosslinkable group on average per molecule, more preferably two or more polymerizable or crosslinkable groups on average per molecule. Because each polymerizable group will polymerize into a chain, crosslinked materials can be produced using only slightly more than one reactive group per polymer (i.e., about 1.02 polymerizable groups on average).

Details of Third Embodiment of Crosslinkable Prepolymer

The third embodiment of the crosslinkable prepolymer is disclosed in WO01/74411 (US designated), the specification of which is hereby incorporated by reference in its entirety. Specifically, it is a crosslinkable multifunctional prepolymer comprising at least two polymerizable terminal groups and having a viscosity such that the crosslinkable prepolymer is deformable at a temperature of 0° to 60° C. into a three-dimensional shape and being crosslinkable within the temperature range. Preferably, the crosslinkable prepolymer comprises a hydrophilic region, at least one biodegradable region and at least one polymerization region and has from 1 to about 100, more preferably from 1 to 20, most preferably 1 to 10, repeating units. The hydrophilic region preferably is a polyethylene glycol or a copolymer of ethylene oxide and an alkylene oxide with a degree of polymerization in the range of 2 to 500.

The crosslinkable prepolymer may comprise a polyacetal sequence; a polyester sequence, resulting from copolymerizing a mixture of lactones wherein none of the lactone comonomers is present in the resulting polyester sequence in a molar proportion above 75%; or a polyorthoester sequence; or a combination of a polyester sequence and a polyorthoester sequence. The polymerizable region of the crosslinkable prepolymer contains alkenes, alkynes or both.

Ratio of Bone Substitute to Crosslinkable Prepolymer

The ratio of the bone substitute to crosslinkable prepolymer in the curable admixture may be a wide range of values. Preferably, the ratio is from 1:20 to 20:1; more preferably from 1:2 to 2:1; most preferably at about 1:1.

Optional Components

The curable admixture and/or cured composite of the present invention may contain the following optional components.

Initiators

In a preferred embodiment, the curable admixture contains free-radical initiators such as photoinitiators, thermally activated initiators, redox initiator systems, ionic initiators or mixture thereof. Any free-radical initiators or combination of initiators can be used. In a first preferred embodiment, one or more photoinitiator(s) is used. In a second preferred embodiment, one or more redox initiator system(s) is used. In a third preferred embodiment, one or more thermal initiator(s) is used. In a fourth preferred embodiment, one or more photoinitiator(s) is used in combination with one or more redox initiator system(s). In a fifth preferred embodiment, one or more thermal initiator(s) is used in combination with one or more redox initiator system(s). In a sixth embodiment, one or more photoinitiator(s) is used in combination with one or more thermal initiator(s). In a seventh preferred embodiment, one or more photoinitiator(s) and one or more thermal initiator(s) are used in combination with one or more redox initiator system(s).

The concentration of the initiator(s) used depends a number of factors. Non-limiting examples of such factors include the type of the initiator, whether the initiator is used alone or in combination with other initiators, the desirable rate of curing, and how the material is applied. In a preferred embodiment, the concentration of the initiator is between about 0.05% (w/w) to about 5% (w/w) of the crosslinkable prepolymer. For photoinitiator(s) or redox initiator system(s), the concentration of the initiator(s) is preferably less than 1% (w/w) of the crosslinkable prepolymer; more preferably between 0.05 and 0.1% (w/w). For thermal initiator(s), the preferred range is about 1% (w/w) to about 2% (w/w) of the crosslinkable prepolymer.

Photoinitiator

A photoinitiator is an initiator activated by radiation. Such radiation could be ultraviolet light (e.g., long wavelength ultraviolet light), light in the visible region, focused laser light, infra-red and near-infra-red light, X-ray radiation or gamma radiation. The preferably radiation is light in the visible region and/or near-infra-red region.

Non-limiting examples of the photoinitiators include biocompatible photoinitiators such as beta carotene, riboflavin, Irgacure 651® (2,2-dimethoxy-2-phenylacetophenone), phenylglycine, dyes such as eosin dye, and initiators such as 2,2-dimethyl-2-phenylacetophenone, 2-methoxy-2-phenylacetophenone, and camphorquinone.

Exposure of dyes and co-catalysts such as amines to light generates active species. Light absorption by the dye causes the dye to assume a triplet state; the triplet state subsequently reacts with the amine to form an active species which initiates polymerization. Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable co-catalysts include amines such as N-methyldiethanolamine, N,N-dimethylbenzylamine, triethanolamine, triethylamine, dibenzyl amine, N-benzylethanolamine, N-isopropylbenzylamine. Triethanolamine is a preferred co-catalyst.

Composition containing photoinitiators is preferably stored in an opaque container.

Redox Initiator System

A redox initiator system includes an oxidizing agent (also called an oxidizing component) (such as a peroxide) and a reducing agent (also called a reducing component) (such as an aromatic or aliphatic amine). Combining the redox couple results in the generation of an initiating species (such as free radicals or cations) capable of causing curing. Preferably, the redox couples of this invention are activated at temperatures below about 40° C., for example, at room temperature or at the physiological temperature of about 37° C. Generally, the redox couple is partitioned into separate reactive compositions prior to use and then subsequently mixed at the time of use to generate the desired initiating species. Selection of the redox couple is governed by several criteria. For example, a desirable oxidizing agent is one that is sufficiently oxidizing in nature to oxidize the reducing agent, but not excessively oxidizing that it may prematurely react with other components with which it may be combined during storage. Similarly, a desirable reducing agent is one that is sufficiently reducing in nature to readily react with the preferred oxidizing agent, but not excessively reducing in nature such that it may reduce other components with which it may be combined during storage. Oxidation or reduction of the resin with an inappropriate reducing agent or oxidizing agent, respectively, could result in an unstable system that would prematurely polymerize and subsequently provide a limited shelf life. Thus, suitable redox couples individually provide good shelf-life (for example, at least 2 months, preferably at least 4 months, and more preferably at least 6 months in an environment of 5-20° C.), and then, when combined together, generate the desired initiating species for curing or partially curing the curable admixture.

Suitable oxidizing agents include peroxide compounds (i.e., peroxy compounds), including hydrogen peroxide as well as inorganic and organic peroxide compounds (e.g., "per" compounds or salts with peroxoanions). Examples of suitable oxidizing agents include, but are not limited to: peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert butyl peroxide, tetraline peroxide, urea peroxide, and cumene peroxide; hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1, ammonium persulfate, sodium perborate, sodium perchlorate, potassium persulfate, etc.; ozone, ozonides, etc. These oxidizing agents may be used alone or in admixture with one another. Benzoyl peroxide is the preferred oxidizing agent. One or more oxidizing agents may be present in an amount sufficient to provide initiation of the curing process. Preferably, this includes about 0.01 weight percent (wt-%) to about 4.0 wt-%, and more preferably about 0.05 wt-% to about 1.0 wt-%, based on the total weight of all components of the dental material.

A reducing agent has one or more functional groups for activation of the oxidizing agent. Preferably, such functional group(s) is selected from amines, mercaptans, or mixtures thereof. If more than one functional group is present, they may be part of the same compound or provided by different compounds. A preferred reducing agent is a tertiary aromatic amine (e.g., N,N-dimethyl-p-toluidine (DMPT) or N,N-bis (2-hydroxyethyl)-p-toluidine (DHEPT)). Examples of such tertiary amines are well known in the art and can be found, for example, at WO 97/35916 and U.S. Pat. No. 6,624,211. Another preferred reducing agent is a mercaptan, which can include aromatic and/or aliphatic groups, and optionally polymerizable groups. Preferred mercaptans have a molecular weight greater than about 200 as these mercaptans have less intense odor. Other reducing agents, such as sulfinic acids, formic acid, ascorbic acid, hydrazines, and salts thereof, can also be used herein to initiate free radical polymerization.

If two or more reducing agents are used, they are preferably chosen such that at least one has a faster rate of activation than the other(s). That is, one causes a faster rate of initiation of the curing of the curable admixture than the other(s).

Electrochemical oxidation potentials of reducing agents and reduction potentials of oxidizing agents are useful tools for predicting the effectiveness of a suitable redox couple. For example, the reduction potential of the oxidant (i.e., oxidizing agent) benzoyl peroxide is approximately −0.16 volts vs. a saturated calomel electrode (SCE). Similarly, the oxidation potential (vs. SCE) for a series of amines has been previously established as follows: dihydroxyethyl-p-toluidine ((DHEPT), 0.76 volt), 4-t-butyl dimethylaniline ((t-BDMA), 0.77 volt), 4-dimethylaminophenethanol ((DMAPE), 0.78 volt), triethylamine ((TEA, 0.88 volt), 3-dimethylaminobenzoic acid ((3-DMAB) 0.93 volt), 4-dimethylaminobenzoic acid ((4-DMAB, 1.07 volts), ethyl p-dimethylaminobenzoate ((EDMAB), 1.07 volts), 2-ethylhexyl p-dimethylaminobenzoate ((EHDMAB), 1.09 volts) and 4-dimethylaminobenzoate ((DMABA), 1.15 volts). The ease of oxidation (and subsequent reactivity) increases as the magnitude of the oxidation decreases. Suitable amine reducing agents in combination with benzoyl peroxide generally include aromatic amines with reduction potentials less than about 1.00 volt vs. SCE. Less effective oxidants than benzoyl peroxide such as lauroyl peroxide (reduction potential=−0.60 volt) are poorer oxidizing agents and subsequently react more slowly with aromatic amine reducing agents. Suitable aromatic amines for lauroyl peroxide will generally include those less than about 0.80 volt vs SCE.

Thermal Initiator

Non-limiting examples of a thermal initiator include a peroxydicarbonate, persulfate (e.g., potassium persulfate or ammonium persulfate), an azo initiator such as azosisobutyronitrile (AIBN), and various peroxides (e.g., benzoyl peroxide). Thermally activated initiators, alone or in combination with other type of initiators, are most useful where light can not reach (e.g., deep within the curable admixture).

Excipients

One or more excipients may be incorporated into the compositions of the present invention. Non-limiting examples of such excipients include $Ca(OH)_2$, demineralized bone powder or particles, hydroxyapatite powder or particles, coral powder, resorbable and non-resorbable hydroxyapatite, calcium phosphate particles, α-tricalcium phosphate, octacalcium phosphate, calcium carbonate, and calcium sulfate. Preferably, such excipients can neutralize the acid generated during the degradation of a biodegradable polymer and maintain a physiological pH value suitable for bone formation. Preferably, such excipient is alkaline in nature so that it can neutralize the acid generated in the biodegradation process and help to maintain a physiological pH value.

Bone Promoting Agents

One or more substances that promote and/or induce bone formation may be incorporated into the compositions of the present invention.

Non-limiting examples of such bone promoting materials include growth factors such as bone morphogenetic protein ("BMP") (Sulzer Orthopedics), BMP-2 (Genetics Institute/Sofamor Danek), basic fibroblast growth factor (bFGF) (Orquest/Anika Therapeutics), Epogen (Amgen), granulocyte colony-stimulating factor (G-CSF) (Amgen), Interleukin growth factor (IGF)-1 (Celtrix Pharmaceuticals), osteogenic protein (OP)-1 (Creative BioMolecules/Stryker Biotec), platelet-derived growth factor (PDGF) (Chiron), stem cell proliferation factor (SCPF) (University of Florida/Advanced Tissue Sciences), recombinant human interleukin (rhIL) (Genetics Institute), transforming growth factor beta (TGRβ) (Collagen Corporation/Zimmer Integra Life Sciences), and TGFβ-3 (OSI Pharmaceuticals). Bone formation may be reduced from several months to several weeks. In orthopedic and dental applications, bone regenerating molecules, seeding cells, and/or tissue can be incorporated into the compositions. For example bone morphogenic proteins such as those described in U.S. Pat. No. 5,011,691, the disclosure of which is incorporated herein by reference, can be used in these applications.

Porosity Forming Agents

One or more substances that promote pore formation may be incorporated into the composition of the present invention; preferably in the curable composite.

Non-limiting examples of such substances include: particles of inorganic salts such as NaCl, $CaCl_2$, porous gelatin, carbohydrate (e.g., monosaccharide), oligosaccharide (e.g., lactose), polysaccharide (e.g., a polyglucoside such as dextrane), gelatin derivative containing polymerizable side groups, porous polymeric particles, waxes, such as paraffin, bees wax, and carnuba wax, and wax-like substances, such as low melting or high melting low density polyethylene (LDPE), and petroleum jelly. Other materials include hydrophilic materials such as PEG, alginate, bone wax (fatty acid dimers), fatty acid esters such as mono-, di-, and tri-glycerides, cholesterol and cholesterol esters, and naphthalene. In addition, synthetic or biological polymeric materials such as proteins can be used.

The size or size distribution of the porosity forming agent particles used in the invention can vary according to the specific need. Preferably the particle size is less than about 5000 μm, more preferably between about 500 and about 5000 μm, even more preferably between about 25 and about 500 μm, and most preferably between about 100 and 250 μm.

Therapeutic Agents

One or more preventive or therapeutic active agents and salts or esters thereof may be incorporated into the compositions of the present invention, including but not limited to:

1) antipyretic analgesic anti-inflammatory agents (which are discussed in greater detail, with additional examples, below), including non-steroidal anti-inflammatory drugs (NSAIDs) such as indomethacin, aspirin, diclofenac sodium, ketoprofen, ibuprofen, mefenamic acid, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone or etodolac; and steroidal drugs such as dexamethasone, dexamethasone sodium sulfate, hydrocortisone, prednisolone;

2) antibacterial and antifungal agents such as penicillin, ampicillin, amoxicillin, cefalexin, erythromycin ethylsuccinate, bacampicillin hydrochloride, minocycline hydrochloride, chloramphenicol, tetracycline, erythromycin, fluconazole, itraconazole, ketoconazole, miconazole, terbinafine; nlidixic acid, piromidic acid, pipemidic acid trihydrate, enoxacin, cinoxacin, ofloxacin, norfloxacin, ciprofloxacin hydrochloride, or sulfamethoxazole trimethoprim; and 3) anti-viral agents such as trisodium phosphonoformate, didanosine, dideoxycytidine, azido-deoxythymidine, didehydro-deoxythymidine, adefovir dipivoxil, abacavir, amprenavir, delavirdine, efavirenz, indinavir, lamivudine, nelfinavir, nevirapine, ritonavir, saquinavir or stavudine;

4) high potency analgesics such as codeine, dihydrocodeine, hydrocodone, morphine, dilandid, demoral, fentanyl, pentazocine, oxycodone, pentazocine or propoxyphene; and 5) salicylates which can be used to treat heart conditions or as an anti-inflammatory.

The agents can be incorporated in the composition directly, or can be incorporated in microparticles which are then incorporated in the composition. Incorporating the agents in microparticles can be advantageous for those agents which are reactive with one or more of the components of the composition.

Diagnostic Agents

One or more diagnostic agents may be incorporated into the compositions of the present invention. Diagnostic/imaging agents can be used which allow one to monitor bone repair following implantation of the compositions in a patient. Suitable agents include commercially available agents used in positron emission tomography (PET), computer assisted tomography (CAT), single photon emission computerized tomography, X-ray, fluoroscopy, and magnetic resonance imaging (MRI).

Examples of suitable agents useful in MRI include the gadolinium chelates currently available, such as diethylene triamine pentaacetic acid (DTPA) and gadopentotate dimeglumine, as well as iron, magnesium, manganese, copper and chromium.

Examples of suitable agents useful for CAT and X-rays include iodine based materials, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte.

These agents can be detected using standard techniques available in the art and commercially available equipment.

Crosslinking the Curable Admixture to Form the Cured Composite

The curable admixture is crosslinked to form the cured composite.

In one embodiment, when a photoinitiator is used (alone or in combination with other type(s) of initiator(s)), the curable admixture is subjected to electromagnetic radiation.

"Electromagnetic radiation" as used herein refers to energy waves of the electromagnetic spectrum including, but not limited to, X-ray, ultraviolet, visible, infrared, far infrared, microwave, radio-frequency, sound and ultrasound waves.

"X-ray" as used herein refers to energy waves having a wavelength of $1 \times 10^{-9}$ to $1 \times 10_{-6}$ cm.

"Ultraviolet light" as used herein refers to energy waves having a wavelength of at least approximately $1.0 \times 10^{-6}$ cm but less than $4.0 \times 10^{-5}$ cm.

"Visible light" as used herein refers to energy waves having a wavelength of at least approximately $4.0 \times 10^{-5}$ cm to about $7.0 \times 10^{-5}$ cm.

"Blue light" as used herein refers to energy waves having a wavelength of at least approximately $4.2 \times 10^{-5}$ cm but less than $4.9 \times 10^{-5}$ cm.

"Red light" as used herein refers to energy waves having a wavelength of at least approximately $6.5 \times 10^{-5}$ cm but less than $7.0 \times 10^{-5}$ cm.

"Infrared" as used herein refers to energy waves having a wavelength of at least approximately $7.0 \times 10^{-5}$ cm.

Audible sound waves are in frequency ranges from 20 to 20,000 Hz.

Infrasonic waves are in frequency ranges below 20 Hz.

Ultrasonic waves are in frequency ranges above 20,000 Hz.

"Radiation source" as used herein refers to a source of electromagnetic radiation. Examples include, but are not limited to, lamps, the sun, blue lamps, and ultraviolet lamps.

The curable admixture is subjected an electromagnetic radiation from a radiation source for a period sufficient to cure the curable admixture and form a cured composite. Preferably, the curable admixture is applied in layer(s) of 1-10 mm, more preferably about 3-5 mm, and subjected to an electromagnetic radiation for about 30 to 300 seconds, preferably for about 50 to 100 seconds, and more preferably for about 60 seconds.

Typically, a minimum of 0.01 mW/cm$^2$ intensity is needed to induce polymerization. Maximum light intensity can range from 1 to 1000 mW/cm$^2$, depending upon the wavelength of radiation. Tissues can be exposed to higher light intensities, for example, longer wavelength visible light, which causes less tissue/cell damage than shortwave UV light. In dental applications, blue light (470-490 nm) is used at intensities of 100 to 400 mW/cm$^2$ clinically. When UV light is used in situ, it is preferred that the light intensity is kept below 20 mW/cm$^2$.

In another embodiment, when a thermally activated initiator is used (alone or in combination with other type(s) of initiator(s)), the curable admixture is subjected to a temperature suitable for activating the thermally activated initiators, preferably the temperature from about 20 to 80° C., more preferably from about 30 to 60° C. Heat required to activate the thermal activator can be generated by various known means, including but not limited to infrared, water bath, oil bath, microwave, ultrasound, or mechanical means. For example, one can place the curable admixture in a crucible heated by a hot water bath.

In yet another embodiment, when a redox initiator system is used (alone or in combination with other type(s) of initiator (s)), the oxidizing agent of the redox initiator system is kept apart from the reducing agent of the redox initiator system until immediately before the curing process. For example, the oxidizing agent is mixed with some curable admixture in one container and the reducing agent is also mixed with some curable admixture in another container. The contents of the two container are mixed with each other at which point substantial curing is initiated.

The curing can take place in situ, ex vivo or in vivo.

In a most preferred embodiment, in order to shorten the duration of the radiation exposure and/or increase the thickness of the each radiation curable layer, a redox initiator system is used in combination with a photoinitiator and/or thermal initiator. For example, the redox initiator system is activated first to partially cure the curable admixture. Such partially cured admixture is then subject to radiation and the photoinitiator and/or thermal initiator is activated to further cure the partially cured admixture.

Property of the Curable Admixture and the Cured Composite

Viscosity

The viscosity of the curable admixture can vary widely. It depends on a number of factors such as the molecular weight of the ingredients in the curable admixture, and the temperature of the curable admixture. Typically, when the temperature is low, the curable admixture is more viscous; and, when the average molecular weight of the ingredients is high, it becomes more viscous. Different applications of the curable admixture also require different viscosities. For example, to be injectable, the admixture must be a free flowing liquid and, in other applications, it must be a moldable paste-like putty.

The viscosity of the curable admixture may be adjusted by formulating the crosslinkable prepolymer with a suitable amount of one or more biocompatible unsaturated functional monomers such as the ones described in WO01/74411(US designated), which are incorporated herein by reference.

Strength

It is preferred that the strength of the cured composite be from about 5 to 300 N/m$^2$; more preferably from about 20 to 200 N/m$^2$; and most desirably from about 50 to 200 N/m$^2$. The strength of the cured composite depends on a number of factors, such as the ratio between the bone substitute and crosslinkable prepolymer, and the crosslinking density of the cured composite.

Hydrophobicity/Hydrophilicity

The hydrophobicity/hydrophilicity of the curable admixture and the cured composite must be carefully controlled. Preferably, the curable admixture and cured composite are sufficiently hydrophilic that cells adhere well to them. The hydrophobicity/hydrophilicity depends on a number of factors such as the hydrophobicity/hydrophilicity of the bone substitute and/or the crosslinkable prepolymer. For example, when the bone substitute is a PMMA/PHEMA based polymer particle, the ratio of PMMA (less hydrophilic) and PHEMA (more hydrophilic) affects the hydrophobicity/hydrophilicity. As another example, if the crosslinkable prepolymer is a polyanhydride instead of a polyethylene glycol, the curable admixture and the cured composite are more hydrophobic.

Biodegradation/Bioresorption Duration

The time needed for biodegradation/bioresorption of the curable admixture and/or the cured composite can be varied widely, from days to years; preferably from weeks to months. The suitable biodegradation/bioresorption duration depends on a number of factors such as the speed of osteointegration, whether the compositions are functional and/or load-bearing, and/or the desirable rate of drug release. For example, osteointegration in an elderly woman is typically much slower than that in a 20 year old man. When osteointegration is slow, a long biodegradation/bioresorption composition should be used. An immediately functional dental implant is load-bearing and must remain strong during osteointegration, so a long biodegradation/bioresorption composition is more suitable for application around such dental implant. If a therapeutic agent is intended to be released over a long period of time, a long biodegradation/bioresorption composition is more suitable.

Depending on the specific application, the time required can be manipulated based on a number of factors, e.g., the ratio of the bone substitute and the crosslinkable prepolymer. When the crosslinkable prepolymer contains more than one type of monomer, the ratio of the monomers also plays a crucial role in the degradation/resorption time. For example, when the crosslinkable prepolymer contains a mixture of dimethacrylated anhydrides of sebacic acid and 1,3-bis(p-carboxyphenxy)-propane, increasing the proportion of dimethacrylated anhydride of sebacic acid decreases the degradation/resorption time. Further, when the bone substitute is PMMA/PHEMA-based (known to be very slowly degradable), increasing the proportion of the bone substitute increases degradation time.

The degradation time is a function of the pH. For example, anhydrides are typically more susceptible to degradation in alkaline condition than in acidic condition.

The degradation time is a function of the hydrophobicity/hydrophilicity of the components. For example, when 1,3-bis(p-carboxyphenxy)-hexane (more hydrophobic) is replaced by 1,3-bis(p-carboxyphenxy)-propane (less hydrophobic), degradation time decreases.

The degradation time is also a function of geometrical shape, thickness, etc.

Where rapid degradation is sought, at least about 15% (w/w), preferably about 50% (w/w), of the cured composite degrades or resorbs in about 5-10 weeks, preferably in about 6-8 weeks.

On the other hand, for slow degradation at least about 15% (w/w), preferably about 50% (w/w), of the cured composite degrades or resorbs in about 6-12 months, preferably in about 9 months.

Application of the Curable Admixture and the Cured Composite

Dental

The curable admixture and cured composite of the present invention can be used to fill extraction sockets; prevent or repair bone loss due to tooth extraction; repair jaw bone fractures; fill bone voids due to disease and trauma; stabilize an implant placed into an extraction socket and one placed into an edentulous jawbone to provide immediate function (e.g., chewing); provide ridge (of bone) augmentation; repair periodontal bone lesions; and provide esthetic gingiva reshaping and plumping. When the curable admixture and/or the cured composite is used for dental implant applications, preferably, the dental implant is partially or fully embedded into the cured composite according one of the following two methods:

Method (1):
(a) planting a dental implant into a bone and/or bone void;
(b) at least partially embedding the dental implant by applying a curable admixture around the dental implant;
(c) curing the curable admixture to form a cured composite; and
(d) repeating steps (b) and (c) if necessary.

Method (2)
(a) at least partially filling a bone void by applying the curable admixture;
(b) curing the curable admixture to form a cured composite;
(c) repeating steps (a) and (b) if necessary;
(d) planting a dental implant into the bone by at least partially embedding the dental implant into the cured composite.

The curable admixture can be crosslinked by exposure to electromagnetic radiation and/or heat and applied using standard dental or surgical techniques. The curable admixture may be applied to the site where bone growth is desired and cured to form the cured composite and cured to form the cured composite. The curable admixture may also be pre-cast into a desired shape and size (e.g., rods, pins, screws, and plates) and cured to form the cured composite.

Orthopedic

The curable admixture and cured composite of the present invention can be used to repair bone fractures, repair large bone loss (e.g., due to disease) and provide immediate function and support for load-bearing bones; to aid in esthetics (e.g., chin, cheek, etc.). The curable admixture can be applied using standard orthopedic or surgical techniques; e.g., it can be applied to a site where bone generation is desired and cured to form the cured composite. The curable admixture may also be pre-cast into a desired shape and size (e.g., rods, pins, screws, plates, and prosthetic devices such as for the skull, chin and cheek) and cured to form the cured composite.

Drug Delivery

The curable admixture and cured composite of the present invention may be used to deliver therapeutic or diagnostic agents in vivo. Examples of drugs or agents which can be incorporated into such compositions include proteins, carbohydrates, nucleic acids, and inorganic and organic biologically active molecules. Specific examples include enzymes, antibiotics, antineoplastic agents, local anesthetics, hormones, angiogenic agents, antiangiogenic agents, antibodies, neurotransmitters, psychoactive drugs, drugs affecting reproductive organs, and oligonucleotides such as antisense oligonucleotides.

EXAMPLES

The following examples are intended to illustrate more specifically the embodiments of the invention. It will be understood that, while the invention as described therein is a specific embodiment, the description and the example are intended to illustrate and not limit the scope of the invention. Other aspects, advantages and modifications within the scope of the invention will be apparent to those skilled in the art to which the invention pertains.

Example 1

This example illustrates the invention with the first embodiment of the crosslinkable prepolymer.

Curable admixtures are formed by mixing two crosslinkable prepolymers: (1) dimethacrylated anhydride of sebacic acid and (2) dimethacrylated anhydride of 1,3-bis(p-carboxyphenoxy) propane) with a bone substitute: (Bioplant® HTR®) as follows.

| Formulation A | |
|---|---|
| Ingredient | Weight |
| dimethacrylated anhydride of sebacic acid | 325 mg |
| dimethacrylated anhydride of 1,3-bis(p-carboxyphenoxy) propane | 175 mg |
| DL-camphoquinone | 5 mg |
| N-phenylglycine | 5 mg |
| Bioplant ® HTR ® | 510 mg |

The dimethacrylated anhydride of sebacic acid is formed by reacting sebacic acid with methacrylic anhydride by heating at reflux and the dimethacrylated anhydride of 1,3-bis(p-carboxyphenoxy) propane is formed by reacting 1,3-bis(p-carboxyphenoxy) propane with methacrylic anhydride by heating at reflux. DL-camphoquinone is used as a photoinitiator. This material is designed to be significantly resorbed in about 6-9 weeks when cured.

| Formulation B | |
|---|---|
| Ingredient | Weight |
| dimethacrylated anhydride of sebacic acid | 175 mg |
| dimethacrylated anhydride of 1,3-bis(p-carboxyphenoxy) propane | 325 mg |
| DL-camphoquinone | 5 mg |
| N-phenylglycine | 5 mg |
| Bioplant ® HTR ® | 510 mg |

This material is designed to be significantly resorbed in about 9 months.

Example 2

This example illustrates the invention with the second embodiment of the crosslinkable prepolymer.

| Formulation C | |
|---|---|
| Ingredient | Weight |
| dimethacrylated anhydride of sebacic acid | 125 mg |
| dimethacrylated anhydride of 1,3-bis(p-carboxyphenoxy) propane | 125 mg |
| Poly(1,3-bis(p-carboxyphenoxy) propane: sebacic acid) (80:20) | 250 mg |
| Irgacure 651 (Ciba-Geigy) | 1 mg |
| Bioplant ® HTR ® | 501 mg |

Poly(1,3-bis(p-carboxyphenoxy) propane: sebacic acid) (80:20) ("Poly(CPP:SA) (80:20)") is a 80:20 (molar ratio) linear co-polymer of 1,3-bis(p-carboxyphenoxy) propane and sebacic acid. It is synthesized according to the procedure described in the Rosen et al. *Biomaterials*, 4, 131, (1983); Domb and Langer, *J. Polym. Sci.*, 23, 3375, (1987).

Example 3

This example illustrates the invention with the third embodiment of the crosslinkable prepolymer. The formulations are examples of a curable admixture formed by mixing (1) a crosslinkable prepolymer having at least two polymerizable terminal groups and a hydrophilic region with (2) bone substitute.

| Formulation D | |
|---|---|
| Ingredient | Weight |
| polyester bis-methacrylate | 254.6 mg |
| demineralized bone powder | 256.2 mg |
| DL-camphoquinone | 4.42 mg |
| N-phenylglycine | 2.54 mg |
| Bioplant ® HTR ® | 517.76 mg |

The polyester bis-methacrylate is prepared according to the method described in Example 1 of WO01/74411.

| Formulation E | |
|---|---|
| Ingredient | Weight |
| poly(D,L-lactide$_{50}$-co-$\epsilon$-caprolactone)-hexanediol$_{20/1}$-methacrylate | 250 mg |
| α-tricalcumphosphate | 250 mg |
| DL-camphorquinone | 1.2 mg |
| N-phenylglycine | 1.1 mg |
| Bioplant ® HTR ® | 502.3 mg |

The poly(D,L-lactide$_{50}$-co-$\epsilon$-caprolactone)-hexanediol$_{20/1}$-methacrylate is prepared according to the method described in WO 01/74411.

Example 4

The following experiment was conducted to study the bone ingrowth after extraction of molars and immediate fixation of an implant and placement of the curable admixture of the present invention. Formulation D of Example 3 was used.

Seven female sheep, ages 3 to 5 years, and thus having mature dentition, were used in the experiment. Two weeks prior to the extraction of teeth, the general health and dentition of the sheep were examined. If necessary, medication was used for de-vermification. Two days prior to the extraction, lateral and oblique pre-operation X-rays of the teeth to be removed were taken. One day prior to extraction, feeding was stopped and prophylactic AB (Excenel® RTU) and NSAID (Finadyne®) were administered. The next day (day 0) the P3 and P4 molars were extracted from both the left and right mandibles of the sheep. Preoperative medication of AB (Excenel® RTU) and Methylprednisolon (0.5 mg/kg, IM) was administered. The curable admixture in Example 3, Formulation D, was applied and cured in layers. The maximum thickness of each layer is about 5 mm. The light source was a standard dental 3M light in the visible light range. For each layer, the light was applied for 80 seconds.

In the left mandible, two titanium implants (Ankylos®), one normal and one modified with a square neck, were placed in one extraction socket. No implant was placed in the other socket. Bioplant® HTR® was mixed with Platelets Rich Plasma (PRP) and placed in the first socket around the implants as well as in the socket without implants. Bioplant® HTR® was then combined with the light curable polymer and placed in the first socket around the neck of the implants and in the occlusal part of the second socket without the implants. The strength of the mixture was from about 30 to about 40 $N/m^2$.

In the right mandible, two titanium implants (Ankylos®), one normal and one modified with a square neck, were placed in one extraction socket. No implant was placed in the other socket. Bioplant® HTR® was mixed with marrow bleeding and placed around the implants and in the socket without implants. Bioplant® HTR® was then combined with the light curable polymer and placed around the neck of the implants and in the occlusal part of the socket without the implants.

On days 1-3 AB (Excenel® RTU) (1 mg/kg) was administered. On day 30, 90 and 180 conventional and intra-oral X-rays were taken. On day 180, the sheep were euthanized and biopsies were performed for histological test.

Example 5

The lower anterior incisor of Patient A was falling out due to advanced gingival and bone disease. Pre-operative X-ray (FIG. 1) revealed that there was almost no bone around the tooth (98% gone, bone resorbed because of gem infection). Abscess and infection were observed. The tooth was about 99% mobile and had to be held in place with fingers. If a normal apicoectomy were conducted, the tooth would not have survived (i.e., it would have fallen out).

Figure 2:
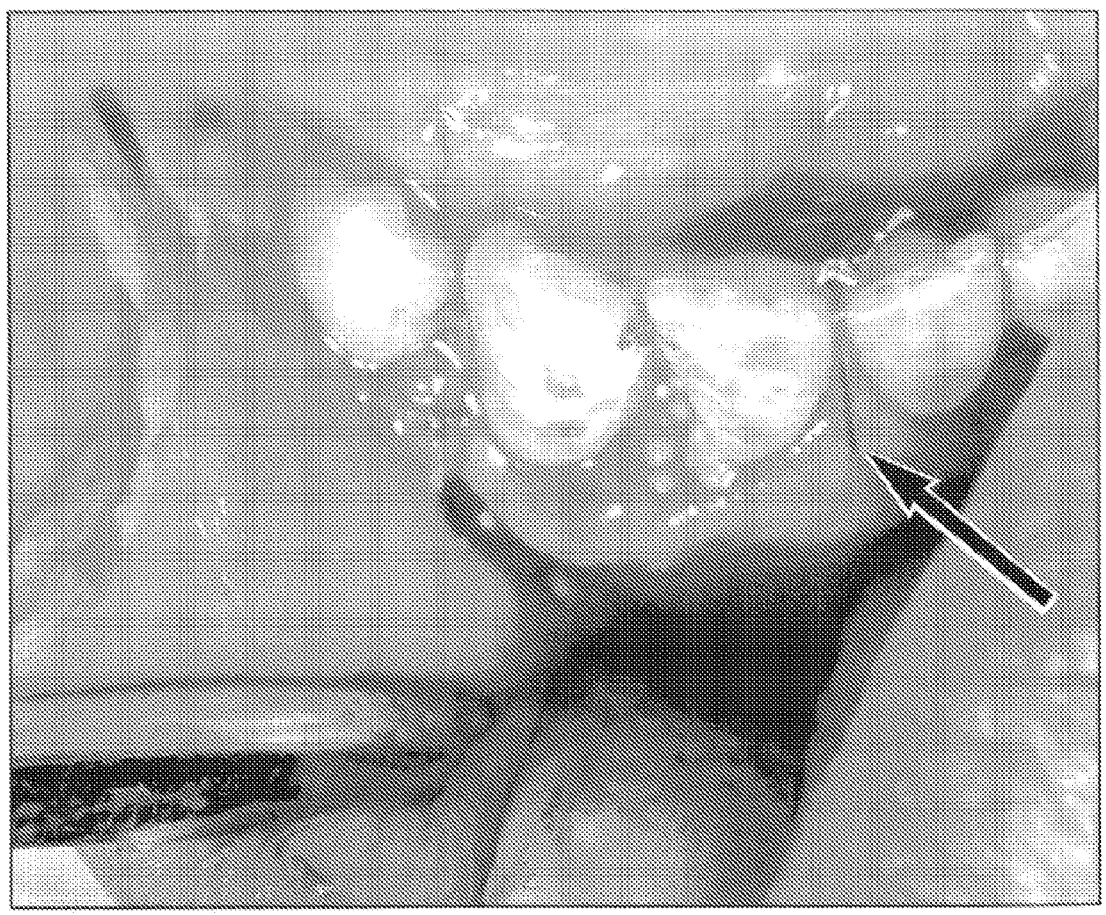
FIG. 2 represents the application of a curable admixture around the lower portion of the tooth in layers of about 5 mm or less and after the desirable thickness was reached, the surgical flap was sutured closed.
Figure 3:
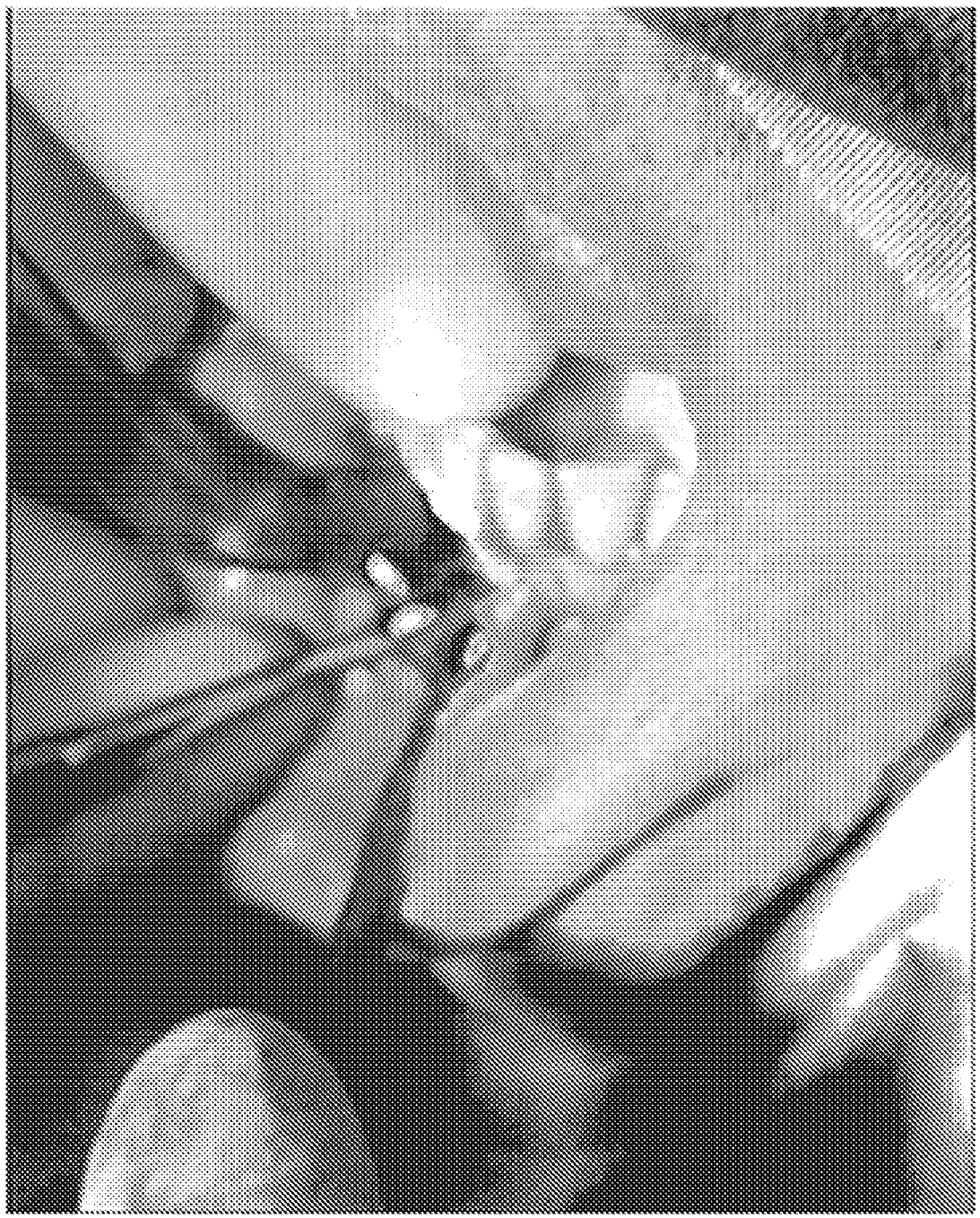
FIG. 3 represents crosslinking/curing the curable admixture in situ with dental light.
Figure 4:
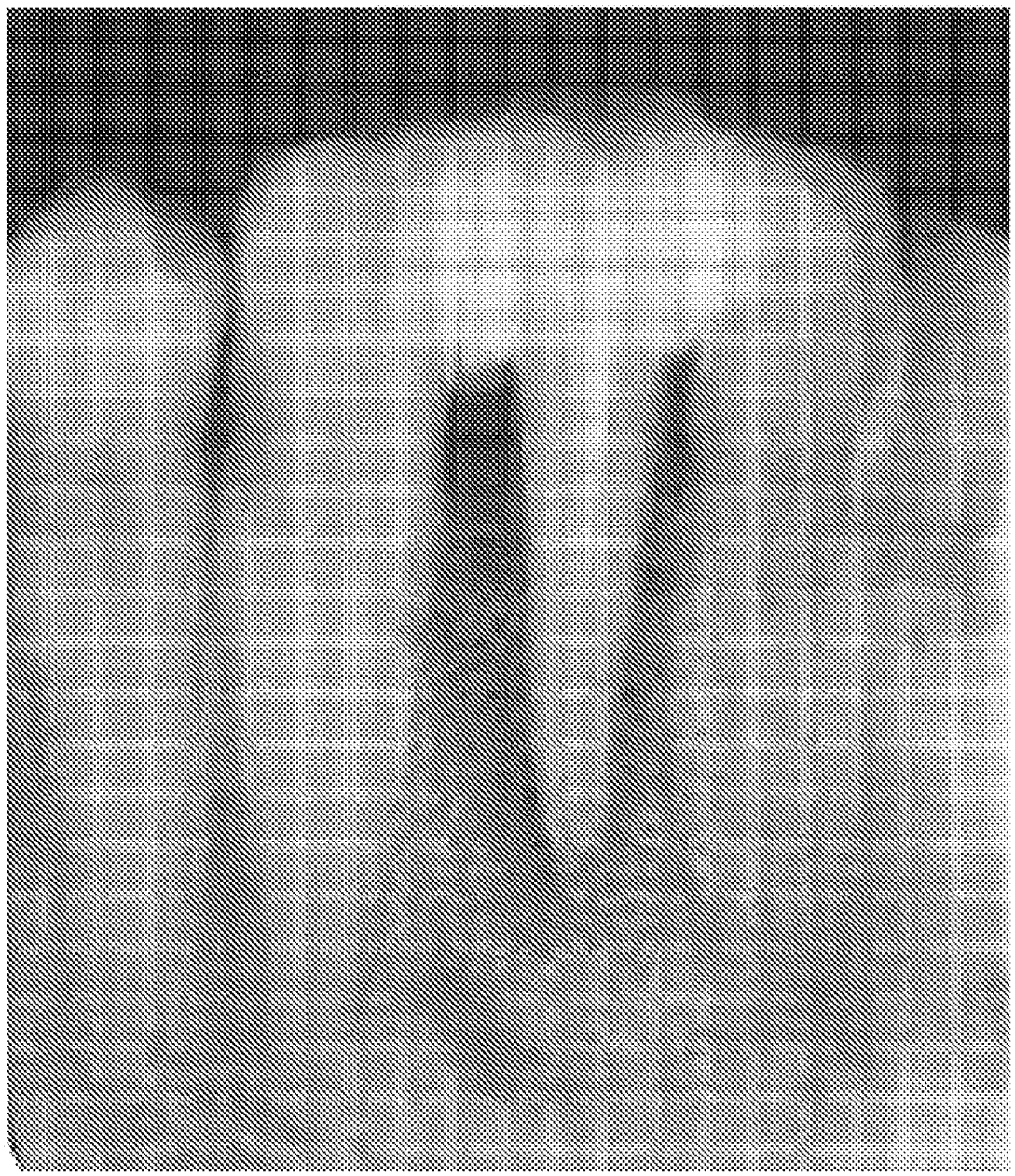
FIG. 4 represents an X-ray taken 20 days after the surgery.
Figure 5:
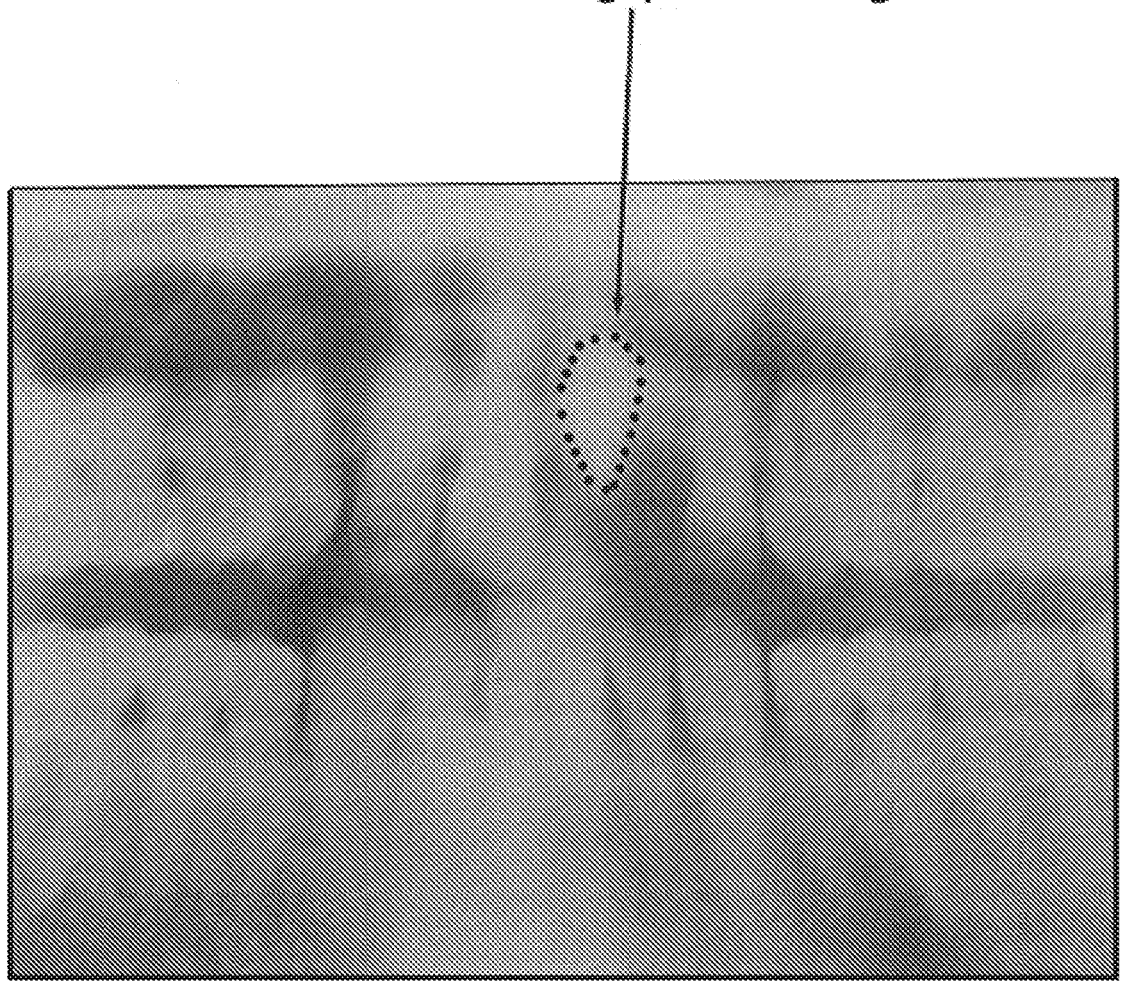
FIG. 5 represents the destruction of the entire buccal plate and the adjacent bone caused by infection and graft failure.
Figure 6:
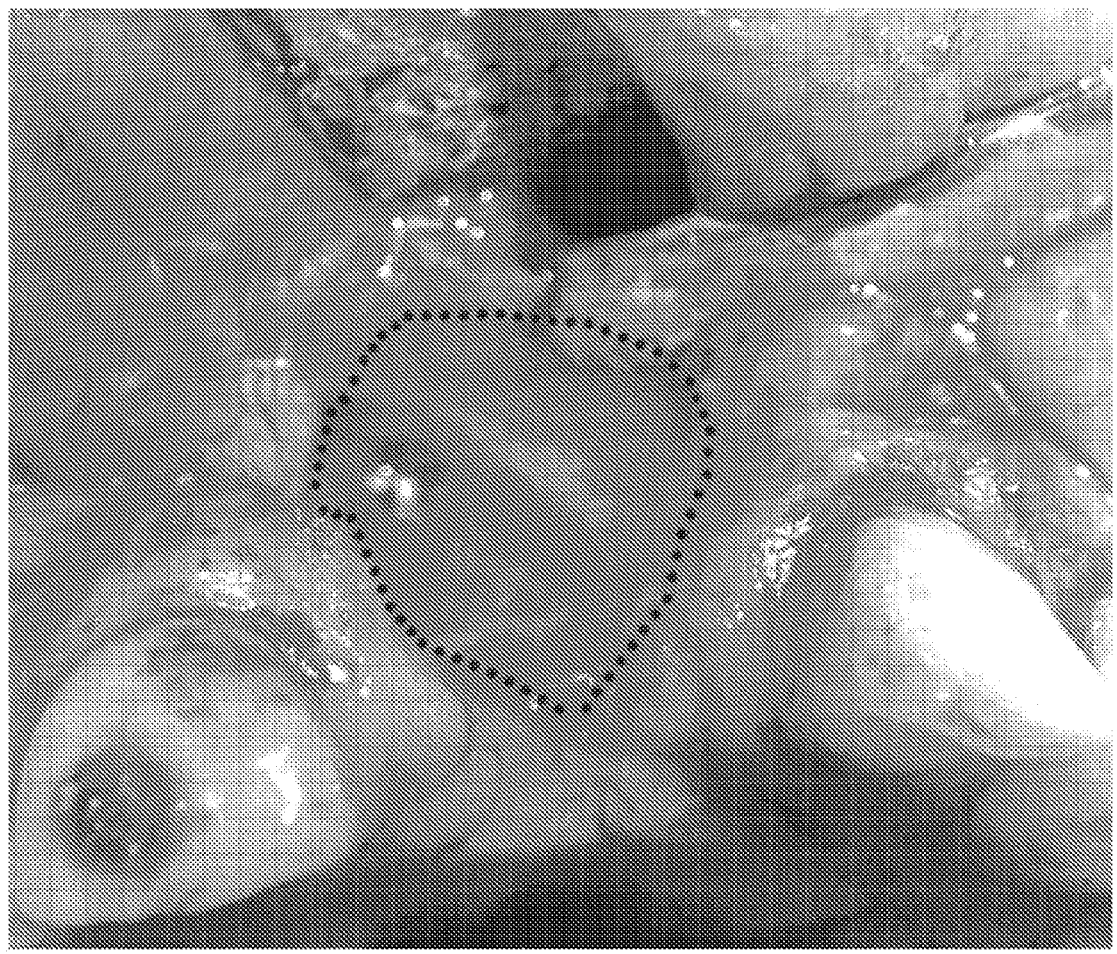
FIG. 6 represents the large bone void revealed after debridement of the area.

After debridement of the area around the tooth, the curable admixture, Formulation D, was applied around the lower portion of the tooth in layers (FIG. 2). Each layer was about 5 mm thick. After the application of each layer, the material in that layer was hardened in situ with blue dental light (source: 3M® Light) for about 80 seconds (FIG. 3). The next layer was applied immediately after the previous layer was hardened. After the desirable stability and thickness was reached and esthetic shape or gingiva was obtained, the surgical flap was repositioned and sutured closed (FIG. 4). The tooth was immediately stable, functional, and free of significant micromovement following the surgery. FIG. 5 is an X-ray taken 20 days after surgery. FIG. 6 is an X-ray taken 3 months after surgery.

Example 6

Figure 7:
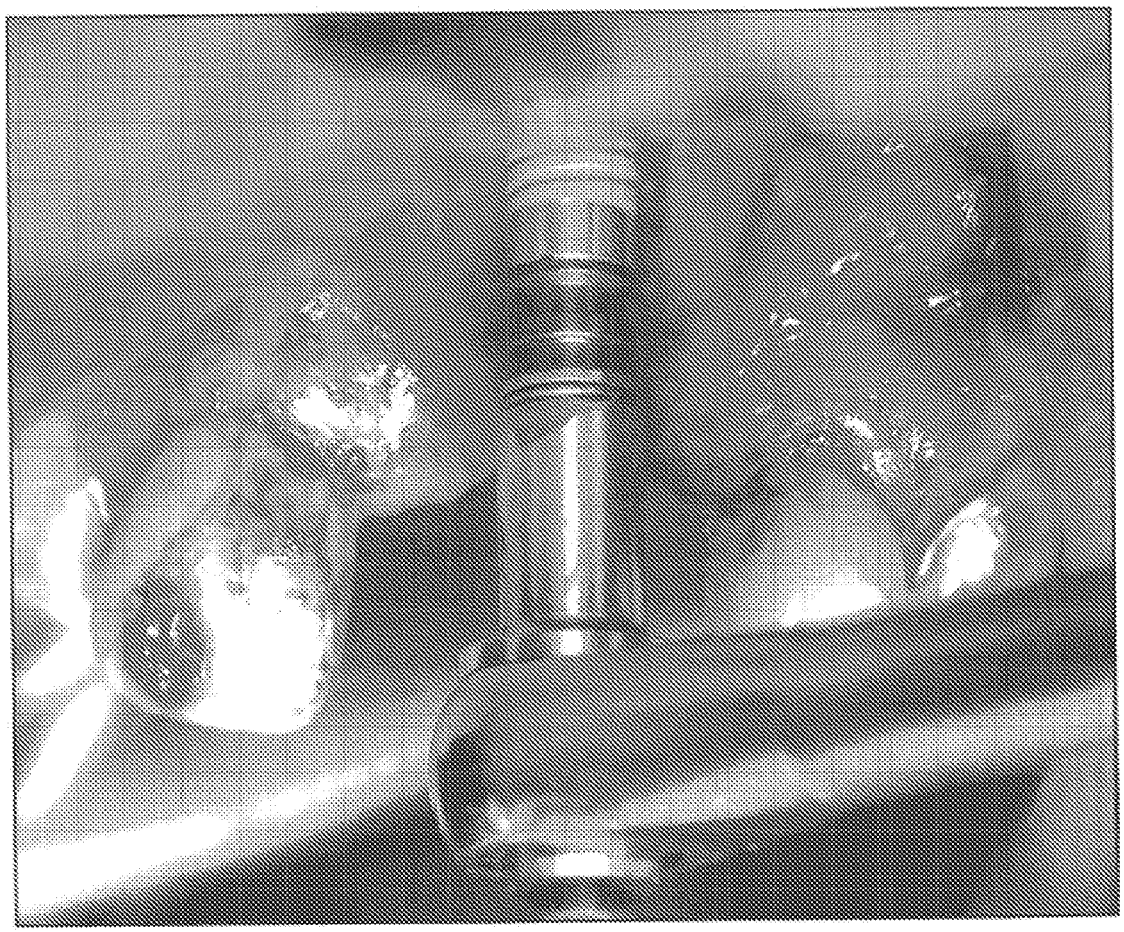
FIG. 7 represents that a metal implant was planted into the bone void with hand instruments.

The upper left central incisor of Patient B had a bone void of 98% due to the tooth extraction and the failed grafting of the socket area with Algipore® (General Medical, UK) graft material. Infection and graft failure resulted not only the loss of a portion of the Algipore® graft, but also the destruction of the entire buccal plate and the adjacent bone (FIG. 7) The failed Algipore® was surrounded by infected soft tissue.

Figure 8:
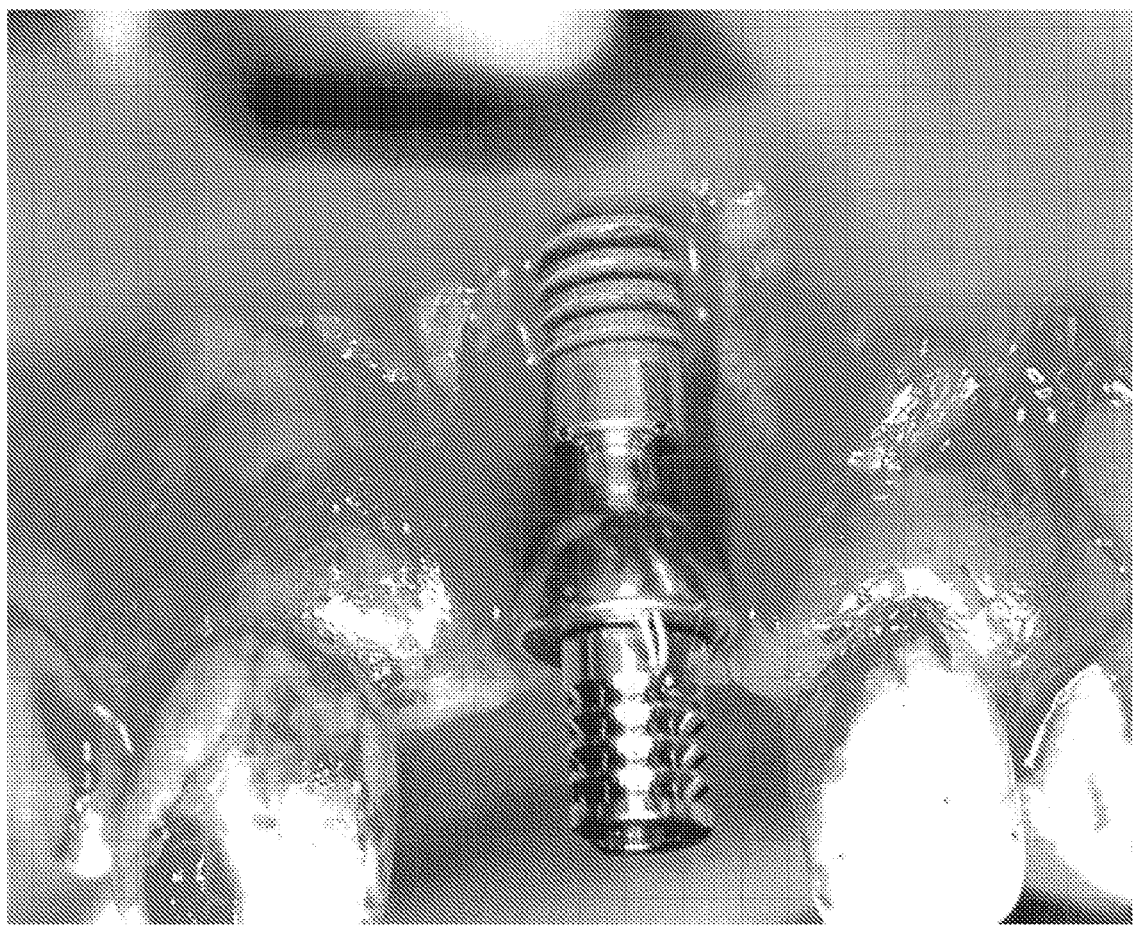
FIG. 8 represents the completed metal implant into the bone void.
Figure 9:
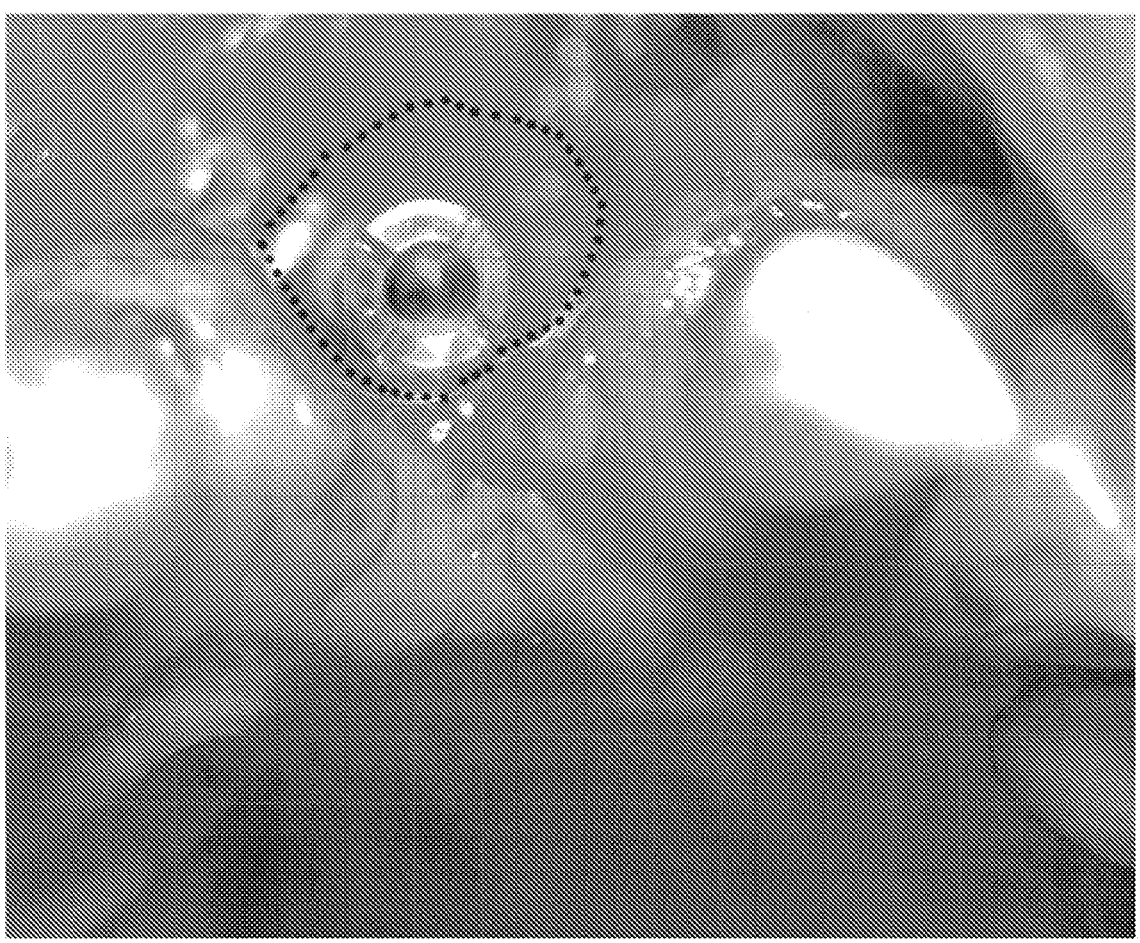
FIG. 9 represents occlusial view of the metal implant and the bone void.
Figure 10:
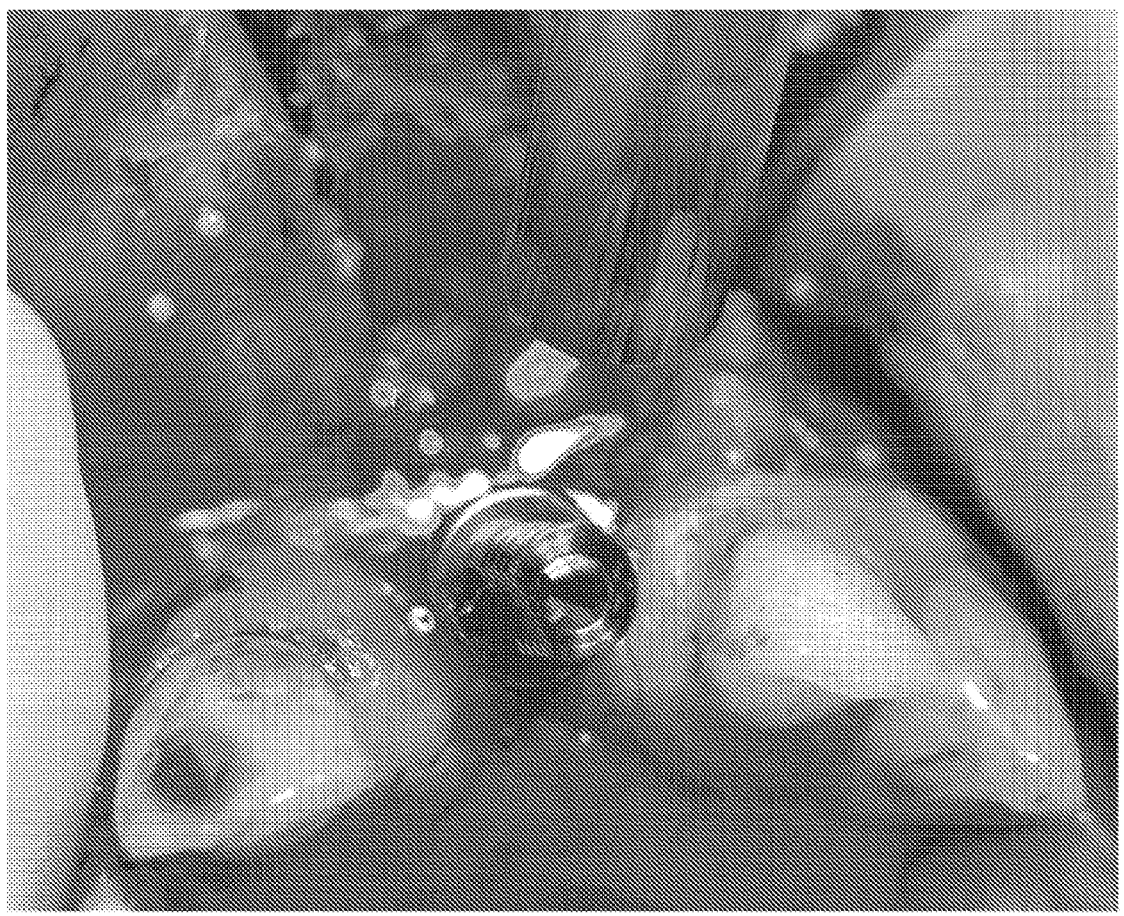
FIG. 10 represents application of a curable admixture around the implant in layers of 5 mm or less and curing of the layer with standard dental light.
Figure 11:
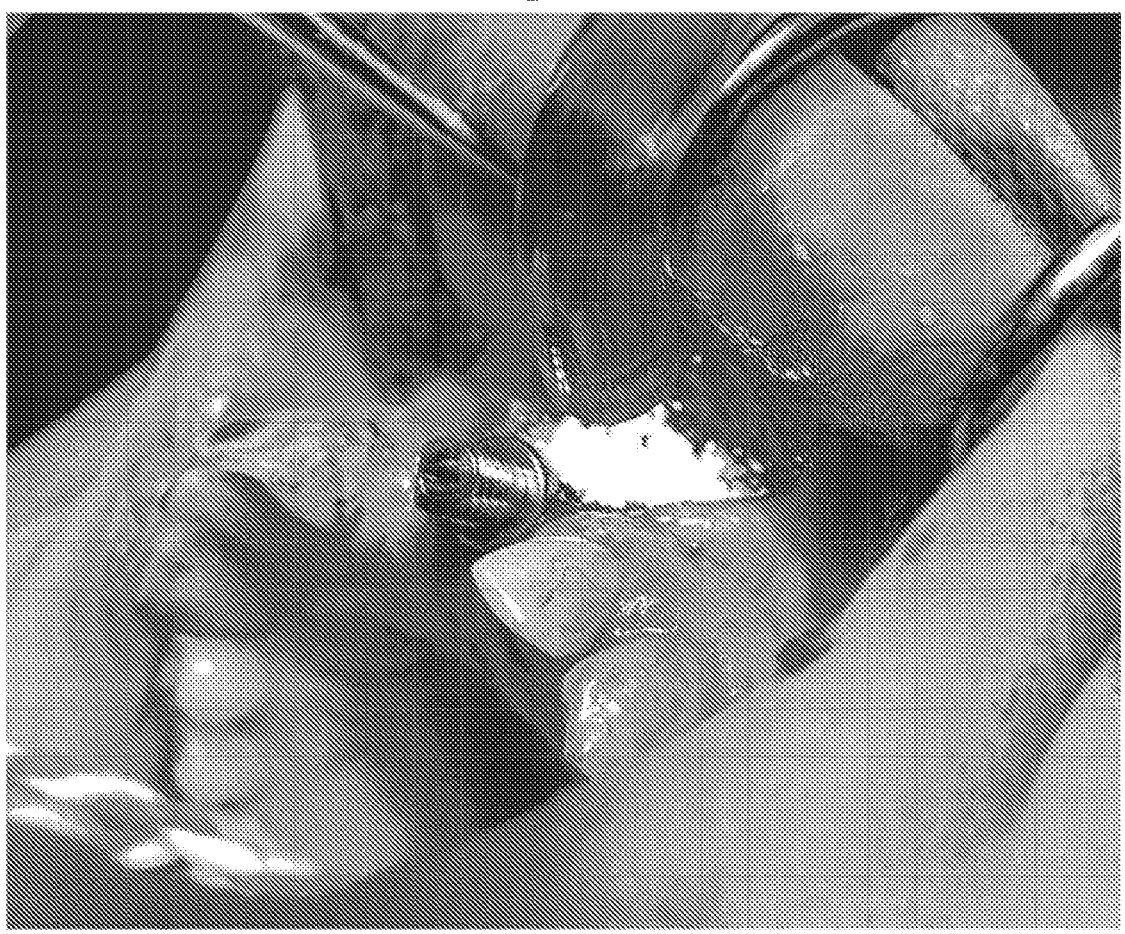
FIG. 11 represents adding and curing the next layer after the previous layer was hardened.
Figure 12:
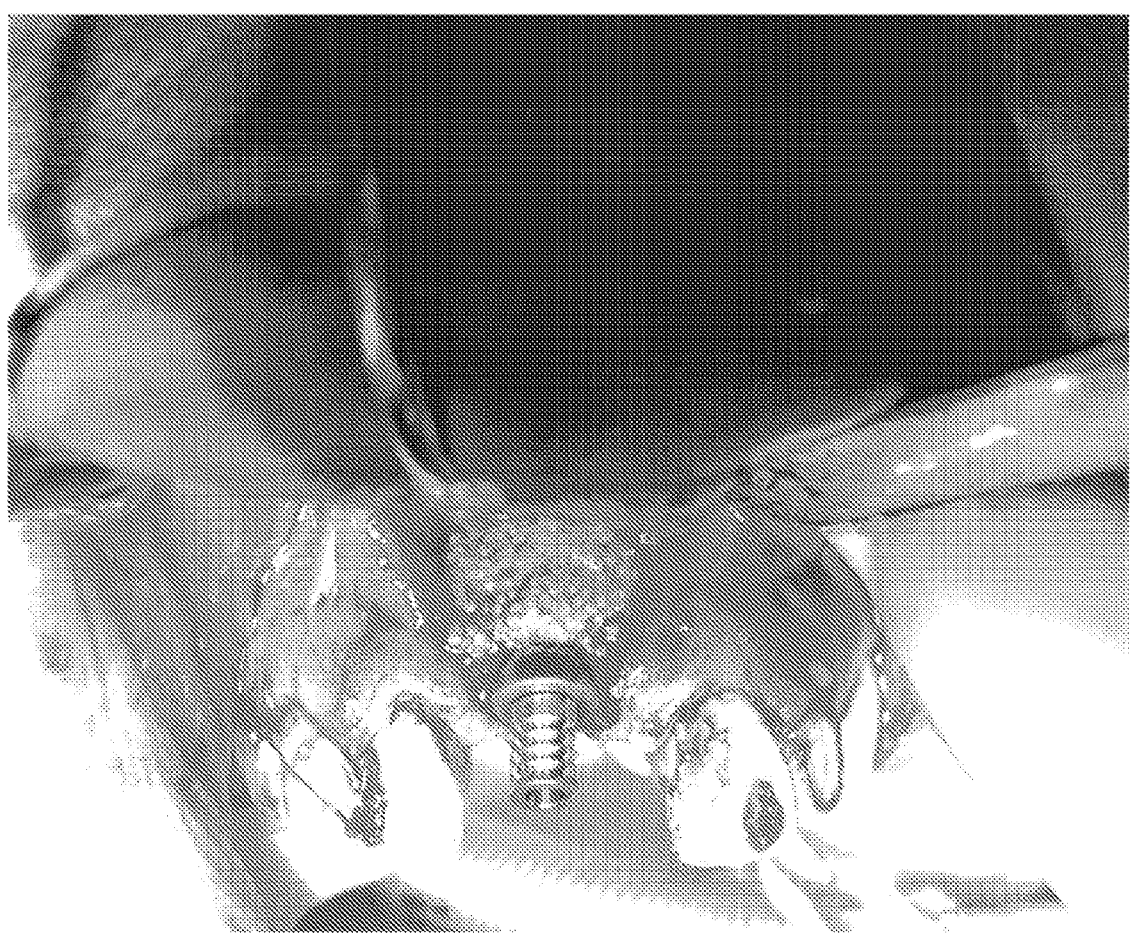
FIG. 12 represents the cured composite of the present invention supporting the metal implant.
Figure 13:
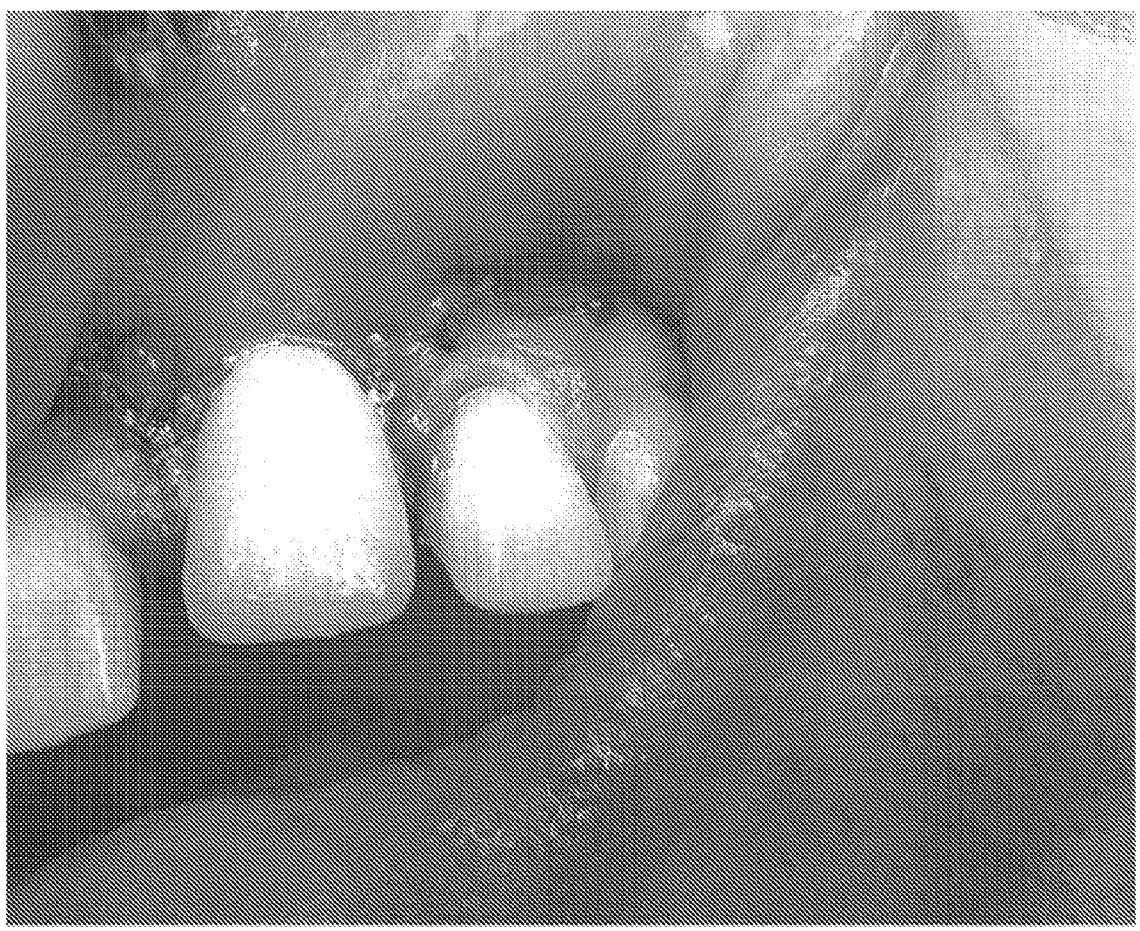
FIG. 13 represents an immediate post-operative temporary jacket added.
Figure 14:
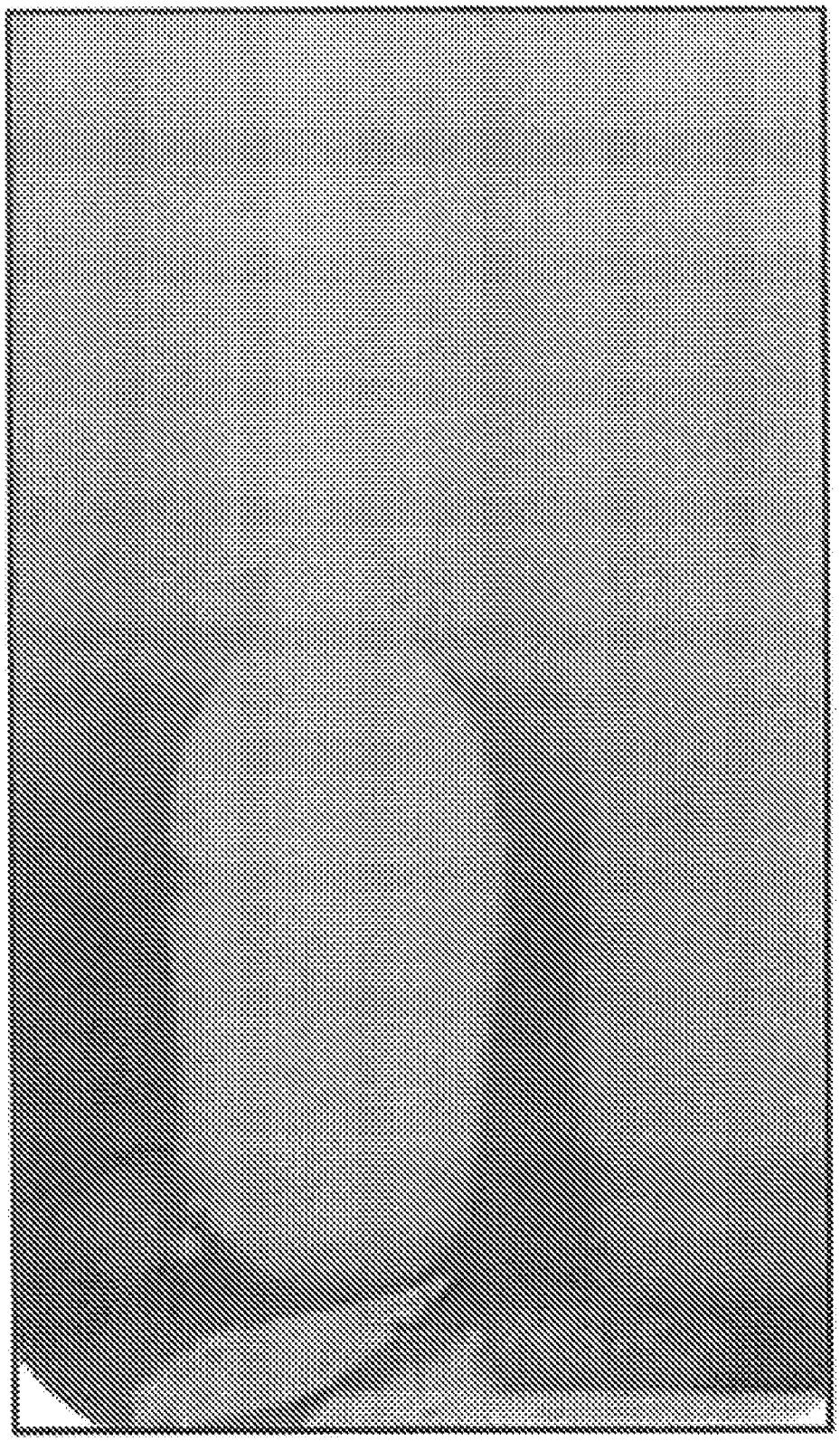
FIG. 14 represents an immediate post-operation X-ray.
Figure 15:
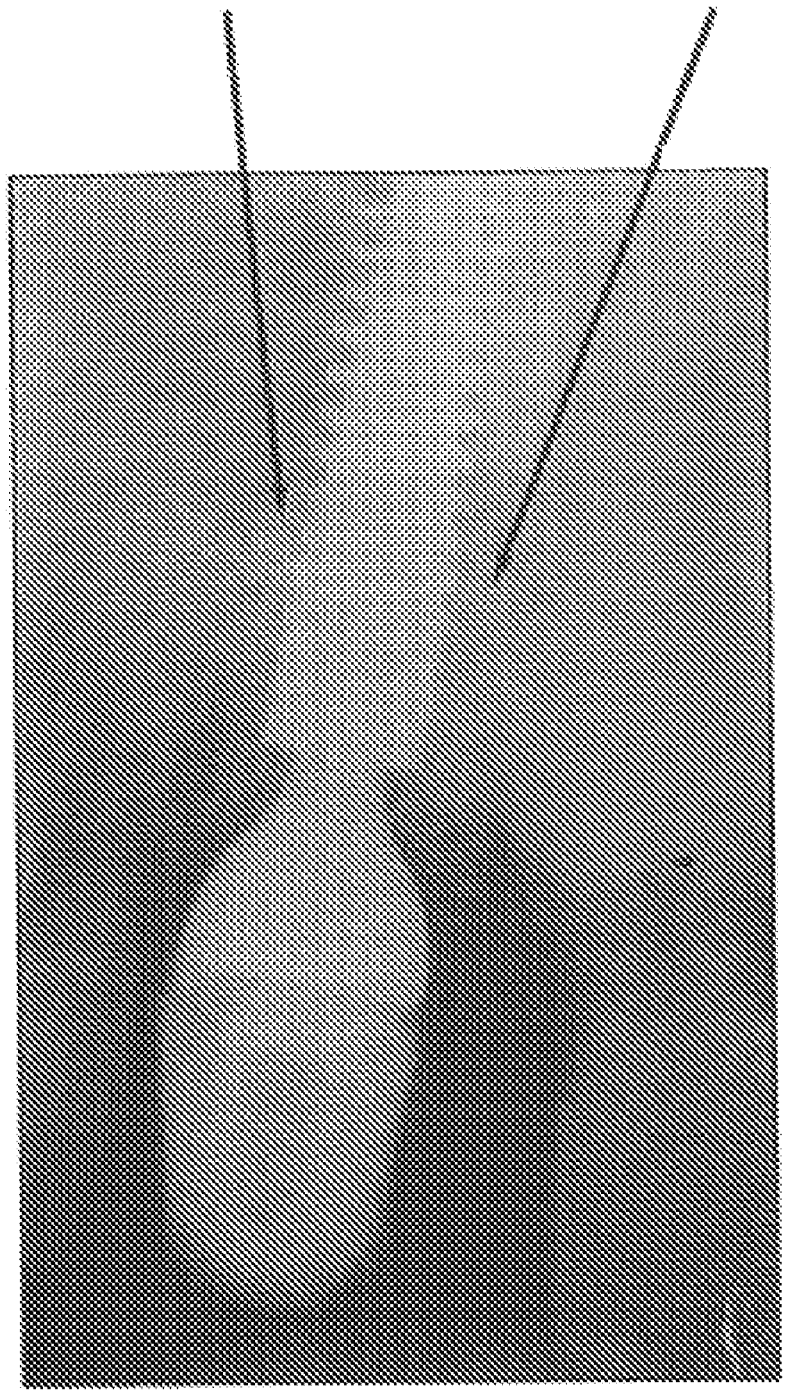
FIG. 15 represents an X-ray taken after the 28th day after the surgery and implantation.

The failed Algipore® was first surgically removed. After debridement of the area, a large bone void was revealed (FIG. 8). A metal implant was planted into the bone void with hand instrumentation (FIG. 9). FIG. 10 shows a picture of the metal implant placed into the bone void being stabilized by bone at the apex of the defect. There was only about 2 mm stabilization bone at the apex. FIG. 11 shows an occlusial view of the metal implant and the extensive bone void. Next, the curable admixture made according to Example 3, Formulation D, was applied around the implant in layers of approximately 5 mm or less and cured (hardened) with standard dental light for about 80 seconds (FIG. 12). After the first layer was hardened, the next layer was added and cured (FIG. 13). More layers were added and cured until the desired thickness for stability and esthetics was reached. FIG. 14 shows a picture of the complete graft with cured material of the present invention (Formulation D) supporting the metal implant. Next, the soft tissue around the implant was sutured. An immediate postoperative temporary jacket was added and placed in function (e.g., contact for chewing) (FIG. 15). FIG. 16 is an immediate post-operation X-ray. The implant was immediately functional, stable, and free of significant micromovement. FIG. 17 is an X-ray taken 28 days after the surgery and implantation. Bone growth was observed around the metal implant. There was no infection.

Example 7

In addition to the synthesis method described in Example 1, methacrylated sebacic acids (MSA) and (1,3-bis(carboxyphenoxy))propyl dimethacrylate (CPPDM) were prepared according to the procedure described by Tarcha et al. *J. Polym. Sci, Part A, Polym. Chem.* (2001), 39, 4189. The MSA was synthesized by reacting sebacyl chloride and methacrylic acid at 0° C. in the presence of triethylamine and dichloromethane. The CPPDM was prepared by reacting methacrylocyl and 1,3-bis(p-caboxyphenoxy) propane (CPP) at 0° C. in the presence of triethylamine and dichloromethane.

Example 8

Samples Prepared

Nine samples were prepared as follows:
(1) 50 wt %:50 wt % LC:HTR (where LC is 100 wt % MSA);
(2) 45 wt %:45 wt %:10 wt % LC:HTR: sucrose (where LC is 100 wt % MSA);
(3) 50 wt %:50 wt % LC:HTR (where LC is 50 wt % MSA and 50 wt % CPPDM);
(4) 75 wt %:25 wt % LC:HTR (where LC is 100 wt % MSA);
(5) 75 wt %:25 wt % LC:HTR (where LC is 90 wt % CPPDM and 10 wt % MSA);
(6) 90 wt %:10 wt % LC: sucrose (where LC is 90 wt % CPPDM and 10 wt % MSA);
(7) 90 wt %:10 wt % LC:HTR (where LC is 90 wt % CPPDM and 10 wt % MSA);
(8) 90 wt %:5 wt %:5 wt % LC:HTR: sucrose (where LC is 90 wt % CPPDM, and 10 wt % MSA); and
(9) 100 wt % LC (where LC 90 wt % CPPDM and 10 wt % MSA).

HTR is abbreviation for Bioplant® HTR®, available from Bioplant Inc. (Norwalk, Conn.).

LC is abbreviation for light curable material. In these 9 samples, LC is MSA, CPPDM, or combination thereof.

MSA is abbreviation for methacrylated sebacic acid:

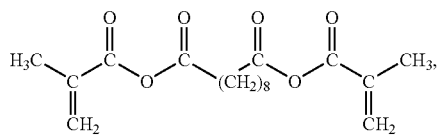

synthesized according to the procedure described by Tarcha et al. *J. Polym. Sci, Part A, Polym. Chem.* (2001), 39, 4189.

CPPDM is abbreviation for (1,3-bis(carboxyphenoxy)) propyl dimethacrylate:

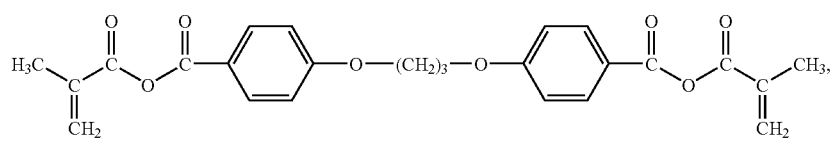

synthesized according to the procedure described by Tarcha et al. *J. Polym. Sci, Part A, Polym. Chem.* (2001), 39, 4189.

Example 9

Photopolyermization

To photopolymerize the samples in Example 8, an initiating system with ethyl 4-dimethylaminobenzoate in conjunction with an equal amount of camphorquinone was used. The ethyl 4-dimethylaminobenzoate and camphorquinone were dissolved in ethanol and added to each of the nine samples of Example 8 at 0.5 wt % relative to the total solids content (LC/HTR/sucrose combined).

The mixture was packed into teflon molds containing 5 mm holes, placed between two glass slides and exposed to a 450 nm visible light source to produce 1 mm thick disks for in vitro degradation experiments (Example 10 below) or 10 mm thick cylinders for in vitro mechanical strength testing (Example 11 below). Such in vitro tests provide good initial assessment as to whether the material would be useful for orthopedic or dental applications. For example, (1) high compressive yield strength indicates that the material is suitable for immediate dental implant purposes, because such dental implants would be able to withstand the biting and/or chewing forces immediately; and (2) percentage of mass loss within a certain time period indicates how fast the material would resorb in vivo and provide a situs for bone/tissue growth.

Example 10

Degradation Experiments

The disks prepared in Example 9 (5 mm in diameter×1 mm in thickness) were placed in individual tubes. The tubes were filled with approximately 1.5 ml of phosphate buffered saline (adjusted to pH 7.4) and the tubes were placed in a shaker incubator thermostatted at 37° C.; the buffer was removed and replaced every 1-2 days. Samples were removed periodically, weighed wet, then dried and reweighed. This allowed for calculation of the equilibrium swelling values as well as the mass loss over time. Data was collected in triplicate.

Example 11

Mechanical Strength Tests

The cylinders prepared in Example 9 (5 mm in diameter× 10 mm in height) were used for the mechanical strength tests. Unconstrained uniaxial compression test were used to evaluate the mechanical properties of the cylinders at room temperature. Standard method was used to calibrate a 500 N load cell before testing. Five specimens of the each sample were mounted on a mechanical analyzer with the calibrated load cell. Specimens that broke at obvious flaws (e.g., water pocket or air pocket formation) were discarded. Strain was calculated from crosshead displacement. Stress was calculated from the load and cross-sectional area.

The ends of the samples were checked to make sure they are parallel to each other. Samples containing sucrose (i.e., Samples 2, 6, and 8) were soaked in de-ionized water overnight right before the testing date. All specimens were tested at 24° C. and ambient humidity.

The diameter of each sample was measured by a caliper to the nearest 0.01 mm at several points along its length. The minimum cross-sectional areas were calculated. The length of each specimen was measured to the nearest 0.01 mm. A concentric semi-circular mold was made to precisely mount the specimen at the center of the bottom anvil. Each specimen was mounted against the semi-circular mold between the surfaces of the anvils of the compression tool. The crosshead of the testing machine was adjusted until it just contacts the top of the compression tool plunger. The speed of the test was set at 1.3±0.3 mm/min. Loads and the corresponding compressive strain at appropriate intervals of strain were recorded to get the complete load-deformation curve. The maximum load carried by each specimen during the test (at the moment of rupture) was also recorded. If a specimen was relatively ductile, the speed was increased to 6 mm/min after the yield point had been reached; and the machine was run at this speed until the specimen breaks. The end point of the test was when the specimen was crushed to failure.

The following properties were calculated: (1) compressive yield strain: strain at the yield point; (2) compressive yield strength: stress at the yield point; and (3) crushing load: the maximum compressive force applied to the specimen, under the conditions of testing, that produces a designated degree of failure.

Example 12

Results and Discussion

The results of the degradation experiment (Example 10) and mechanical strength tests are summarized below.

TABLE 1

Results of testing for LC/BioPlant HTR formulations.

| Sample[1] | LC[2] (wt %) | HTR (wt %) | Sucrose (wt %) | Compressive yield strain (%) | Compressive yield strength (MPa) | Crushing Load (MPa) | Integrity lost (days) | Swelling wt % in water | % Mass loss (# days) |
|---|---|---|---|---|---|---|---|---|---|
| 1 | 50[3] | 50 | 0 | — | 12.59 (±2.441) | — | 4 | slight amount, 50 wt % | 43 ± 2 (20) |
| 2 | 45[3] | 45 | 10 | — | 4.365 (±1.334)[6] | — | 4 | slight amount, 50 wt % | 49 ± 3 (18) |
| 3 | 50[4] | 50 | 0 | — | — | — | 6 | slight amount, 50 wt % | 35 ± 2 (21) |
| 4 | 75[3] | 25 | 0 | — | — | — | 8 | 100 wt % | 62 ± 4 (21) |
| 5 | 75[5] | 25 | 0 | 6.285 (±1.30) | 18.81 (±3.107) | 19.06 (±3.15) | 11 | 50 wt % | 45 ± 2 (44) |
| 6 | 90[5] | 0 | 10 | 5.186 (±0.4822) | 9.295 (±1.249)[6] | 22.44 (±4.908) | 11 | >200 wt % | 56 ± 6 (44) |
| 7 | 90[5] | 10 | 0 | 6.484 (±0.3490) | 23.19 (±1.612) | — | 36 | slight amount, 50 wt % | 40 ± 4 (48) |
| 8 | 90[5] | 5 | 5 | 9.082 (±1.229) | 21.79 (±2.834)[6] | 22.92 (±2.584) | 36 | slight amount, 50 wt % | 47 ± 2 (48) |
| 9 | 100[5] | 0 | 0 | 5.878 (±0.8676) | 11.67 (±3.028) | 14.36 (±4.121) | 56 | 75 wt % after 36 days | 40 ± 3 (36) |

[1]Photopolymerization conditions: 0.5 wt % camphorquinone, 0.5 wt % ethyl 4-dimethylaminobenzoate, λ = 450 nm
[2]MSA = methacrylated sebacic acid, CPPDM = (1,3-bis(carboxyphenoxy))propyl dimethacrylate
[3]composition = 100 wt % MSA
[4]composition = 50 wt % MSA/50 wt % CPPDM
[5]composition = 10 wt % MSA/90 wt % CPPDM
[6]soaked in deionized water to remove sucrose prior to testing These results indicate that the materials of the present invention are suitable for various applications. For example, Samples (1)-(2) are suitable for very short term applications, delivery method for HTR to keep it in place temporarily; Sample (3) is suitable for short term applications and delivery method for HTR to keep it in place temporarily; Sample (4) is suitable for short term applications. The high swelling may lead to good integration and good cellular infiltration; Sample (5) is suitable for longer term applications where stability is needed for healing and integration because its mass loss is significantly slower than that of formulations with more MSA; Sample (6) is suitable for longer term applications where stability is needed for healing and integration because its swelling is significantly more than in any other formulation, which maybe useful for enhanced tissue integration; Sample (7) is suitable for a longer term formulation to promote bone growth while maintaining stability because it lacks swelling and degrades at a slower rate as compared to formulations with higher HTR contents; Sample (8) is suitable for longer term needs where the sucrose is added to allow for cellular infiltration, the presence of the sucrose may help improve tissue integration; and Sample (9) is suitable for systems where stability is vital to success.

Example 13

Multi-Stage Curing

A curable admixture is made according to Formulation F below.

Formulation F

| Ingredient | Weight |
|---|---|
| dimethacrylated anhydride of sebacic acid | 300 mg |
| dimethacrylated anhydride of 1,3-bis(p-carboxyphenoxy) propane | 300 mg |

-continued

Formulation F

| Ingredient | Weight |
|---|---|
| dimethacrylated polyethylene glycol | 400 mg |
| α-tricalcium phosphate | 10 mg |
| CaCO$_3$ | 10 mg |
| CaCl$_2$ | 10 mg |
| DL-camphoquinone | 5 mg |
| N-phenylglycine | 5 mg |
| Bioplant ® HTR ® | 1000 mg |

The curable admixture made according to Formulation F is separated into equal portions: A and B. 5 mg of benzoyl peroxide (oxidizing component of a redox initiator system) is mixed into portion A. The resulting portion A is placed into one barrel of a multi-barrel syringe. 5 mg of N,N-dimethyl-p-toluidine (DMPT) (reducing component of a redox initiator system) is mixed into portion B. The resulting portion B is placed in to another barrel of the multi-barrel syringe.

Contents of the two barrels of the syringe are thoroughly mixed to partially cure the resulting mixture. The partially cured mixture is then applied to the tissue site and further cured by exposure to radiation. Barrel configurations can be either single with two-coaxial barrels or double, where one or both barrel(s) is covered to reduce light penetration.

What is claimed:
1. A composition comprising a curable admixture of
   (A) a polymeric bone substitute which is an autograft, allograft, xenograft or alloplast or mixture thereof;
   (B) a crosslinkable prepolymer comprising
       (i) a linear polymer selected from the group consisting of linear, hydrophobic biodegradable polymers and linear non-degradable hydrophilic polymers; and
       (ii) at least one monomer or macromer containing at least one free radical polymerizable group, wherein at least one of the monomers or macromers includes an anhydride linkage and a polymerizable group selected from the group consisting of acrylate or methacrylate;
(C) a biocompatible photoinitiator; and
(D) one or both parts of a redox system containing an oxidizing component and a reducing component.

2. The composition of claim 1, wherein the monomer or macromer contains 1 to 100 repeating units.

3. The composition of claim 1, wherein the linear hydrophobic biodegradable polymer is formed from one or more units selected from the group consisting of polyanhydrides, polyorthoesters, polyhydroxy acids, polydioxanones, polycarbonates, and polyaminocarbonates.

4. The composition of claim 1, wherein the linear non-degradable hydrophilic polymer is formed from one or more units selected from the group consisting of poly(ethylene glycol), poly(ethylene oxide), partially or fully hydrolyzed poly(vinyl alcohol), poly(ethylene oxide)-co-poly(propylene oxide) block copolymers (poloxamers and meroxapols) and poloxamines.

5. The composition of claim 1 wherein the polymeric bone substitute comprises porous micron-sized particles, each particle having a core layer of a first biocompatible polymeric material and a coating of a second biocompatible polymeric material surrounding the core layer, wherein the second polymeric material is hydrophilic and different in composition from the first polymeric material.

6. The composition of claim 5, wherein the diameter of the micron-sized particles is from about 250 microns to about 900 microns.

7. The composition of claim 5, wherein the polymeric bone substitute further comprising a quantity of calcium hydroxide distributed on the outer surface of and inside the micron-sized particles.

8. The composition of claim 5, wherein the first polymeric material is poly(methylmethacrylate).

9. The composition of claim 5, wherein the second polymeric material is a poly(hydroxyethylmethacrylate).

10. The composition of claim 5, wherein the ratio of the polymeric bone substitute to the crosslinkable prepolymer is from about 1:20 to 20:1.

11. The composition of claim 10, wherein the ratio of the polymeric bone substitute to the crosslinkable prepolymer is from about 1:2 to 2:1.

12. The composition of claim 1, further comprising a therapeutic agent.

13. The composition of claim 1, further comprising either the oxidizing component or the reducing component of a redox initiator system.

14. The composition of claim 1, further comprising a bone promoting agent.

15. The composition of claim 14, wherein the bone promoting agent is a basic fibroblast growth factor.

16. A method of forming a cured composition comprising:
(A) forming a curable admixture of
(i) a polymeric bone substitute which is an autograft, allograft, xenograft or alloplast or mixture thereof;
(ii) a crosslinkable prepolymer comprising
(a) a linear polymer selected from the group consisting of linear, hydrophobic biodegradable polymers and linear non-degradable hydrophilic polymers; and
(b) at least one monomer or macromer containing at least one free radical polymerizable group, wherein at least one of the monomers or macromers includes an anhydride linkage and a polymerizable group selected from the group consisting of acrylate or methacrylate
(iii) a photoinitiator; and
(iv) a redox system comprising an oxidizing component and a reducing component;
(B) partially curing said admixture by the reaction of the two component of the redox system, and
(C) exposing the partially cured curable admixture to sufficient radiation to photopolymerize said partially cured curable admixture.

17. A cured composition formed by curing a composition comprising a curable admixture of a polymeric bone substitute which is an autograft, allograft, xenograft or alloplast or mixture thereof and a crosslinkable prepolymer wherein the crosslinkable prepolymer comprises
(A) a linear polymer selected from the group consisting of linear, hydrophobic biodegradable polymers and linear non-degradable hydrophilic polymers; and
(B) at least one monomer or macromer containing at least one free radical polymerizable group, wherein at least one of the monomers or macromers includes an anhydride linkage and a polymerizable group selected from the group consisting of acrylate or methacrylate,
wherein said curing occurred in the presence of a biocompatible photoinitiator; and one or both parts of a redox system containing an oxidizing component and a reducing component.

18. The cured composition of claim 17, wherein the polymeric bone substitute comprises porous micron-sized particles, each particle having a core layer of a first biocompatible polymeric material and a coating of a second biocompatible polymeric material surrounding the core layer, wherein the second polymeric material is hydrophilic and different in composition from the first polymeric material.

19. The cured composition of claim 17, wherein at least 20% (w/w) of the cured composition biodegrades in from about 6 to 10 weeks.

20. The cured composition of claim 19, wherein at least 50% (w/w) of the cured composition biodegrades in from about 6 to 10 weeks.

21. The cured composition of claim 17, wherein at least 20% (w/w) of the cured composition biodegrades in from about 6 to 12 months.

22. The cured composition of claim 21, wherein at least 50% (w/w) of the cured composition biodegrades in from about 6 to 12 months.

23. The cured composition of claim 17, further comprising a bone promoting agent.

24. The cured composition of claim 23, wherein the bone promoting agent is a basic fibroblast growth factor.

25. A method of promoting bone generation comprising the steps of:
(A) applying to an area in need of such promotion a composition comprising a curable admixture of a polymeric bone substitute which is an auto graft, allograft, xenograft or alloplast or mixture thereof and a crosslinkable prepolymer wherein the crosslinkable prepolymer comprises
(i) a linear polymer selected from the group consisting of linear, hydrophobic biodegradable polymers and linear non-degradable hydrophilic polymers; and
(ii) at least one monomer or macromer containing at least one free radical polymerizable group, wherein at least one of the monomers or macromers includes an anhydride linkage and a polymerizable group selected from the group consisting of acrylate or methacrylate; and (B) curing the compositions, wherein said curing occurred in the presence of a biocompatible photoinitiator; and one or both parts of a redox system containing an oxidizing component and a reducing component.

26. A method of stabilizing a dental implant comprising the step of:
   at least partially embedding a dental implant into a cured composition wherein the cured composition is obtained by curing a curable admixture of a bone substitute which is an autograft, allograft, xenograft or alloplast or mixture thereof and a crosslinkable prepolymer, wherein the crosslinkable prepolymer comprises
   (iii) a linear polymer selected from the group consisting of linear, hydrophobic biodegradable polymers and linear non-degradable hydrophilic polymers; and
   (iv) at least one monomer or macromer containing at least one free radical polymerizable group, wherein at least one of the monomers or macromers includes an anhydride linkage and a polymerizable group selected from the group consisting of acrylate or methacrylate,
   wherein said curing occurred in the presence of a biocompatible photoinitiator; and one or both parts of a redox system containing an oxidizing component and a reducing component.

27. The method of claim 26, wherein the dental implant is at least partially embedded into the cured composition by the steps of:
   (1) planting a dental implant into a bone and/or bone void;
   (2) at least partially embedding the dental implant by applying a curable admixture around the dental implant; and
   (3) curing the curable admixture to form the cured composite.

28. The method of claim 26, wherein the dental implant is at least partially embedded into the cured composition by the steps of:
   (1) at least partially filling a bone void by applying a curable admixture;
   (2) curing the curable admixture to form the cured composite; and
   (3) planting a dental implant into the bone by at least partially embedding the dental implant into the cured composite.

29. A method of preparing objects of desired shape and size comprising the step of: curing in a mold a curable admixture of a bone substitute which is an autograft, allograft, xenograft or alloplast or mixture thereof and a crosslinkable prepolymer, wherein the crosslinkable prepolymer comprises
   (i) a linear polymer selected from the group consisting of linear, hydrophobic biodegradable polymers and linear non-degradable hydrophilic polymers; and
   (ii) at least one monomer or macromer containing at least one free radical polymerizable group, wherein at least one of the monomers or macromers includes an anhydride linkage and a polymerizable group selected from the group consisting of acrylate or methacrylate,
   wherein said curing occures in the presence of a biocompatible photoiitiator; and one or both parts of a redox system containing an oxidizing component and a reducing component.

30. A method of drug delivery comprising the steps of:
   (A) applying to an area in need of drug delivery a composition comprising a curable admixture of a bone substitute which is an autograft, allograft, xenograft or alloplast or mixture thereof and a crosslinkable prepolymer, and a therapeutic agent,
   wherein the crosslinkable prepolymer comprises
      (i) a linear polymer selected from the group consisting of linear, hydrophobic biodegradable polymers and linear non-degradable hydrophilic polymers; and
      (ii) at least one monomer or macromer containing at least one free radical polymerizable group, wherein at least one of the monomers or macromers includes an anhydride linkage and a polymerizable group selected from the group consisting of acrylate or methacrylate; and
   (B) curing the composition, wherein said curing occurred in the presence of a biocompatible photoinitiator; and one or both parts of a redox system containing an oxidizing component and a reducing component.

* * * * *